United States Patent [19]

Fukuyama

[11] 4,109,508

[45] Aug. 29, 1978

[54] METHOD OF DETECTING A SURFACE FLAW OF METALLIC MATERIAL

[75] Inventor: Masaru Fukuyama, Himeji, Japan

[73] Assignee: Nipponn Steel Corporation, Tokyo, Japan

[21] Appl. No.: 682,023

[22] Filed: Apr. 30, 1976

[30] Foreign Application Priority Data

Jun. 26, 1975 [JP] Japan ................................. 50-79905

[51] Int. Cl.² ......................................... G01N 25/72
[52] U.S. Cl. ................................................ 73/15 FD
[58] Field of Search .................. 73/15 R, 15 F, 15 D, 73/104; 250/341

[56] References Cited

U.S. PATENT DOCUMENTS

| | | | |
|---|---|---|---|
| 3,020,745 | 2/1962 | Sielicki | 73/15 |
| 3,378,685 | 4/1968 | Green et al. | 73/15 |
| 3,672,204 | 6/1972 | Green | 73/15 |
| 3,681,970 | 8/1972 | Wells | 73/15 |
| 3,805,073 | 4/1974 | Jayachandrax | 250/341 |

OTHER PUBLICATIONS

Green, "Thermal & Infrared Nondestructive Testing of Composites & Ceramics in Materials Evaluation", vol. 29, #1, 11/71 pp. 241-249.

*Primary Examiner*—Herbert Goldstein

[57] ABSTRACT

A method for detecting a surface defect or flaw of metallic material, comprising the steps of subjecting the surface layer of metallic material to high-frequency induction heated in a linear manner, transferring the heating portion of the surface layer of the metallic material, measuring the surface temperature of the metallic material after its being subjected to heating, and determining the depth of the surface defect or flaw on the basis of the level of the value of temperature rise.

6 Claims, 18 Drawing Figures

| CLASSIFICATION OF SURFACE FLAW | | SHAPE OF SURFACE FLAW | RESULT OF VISUAL INSPECTION |
|---|---|---|---|
| CRACK | SMALL-SIZED | | |
| | LARGE-SIZED | | |
| | HEXAGONAL | | |
| OSCILLATION CRACK | | | |

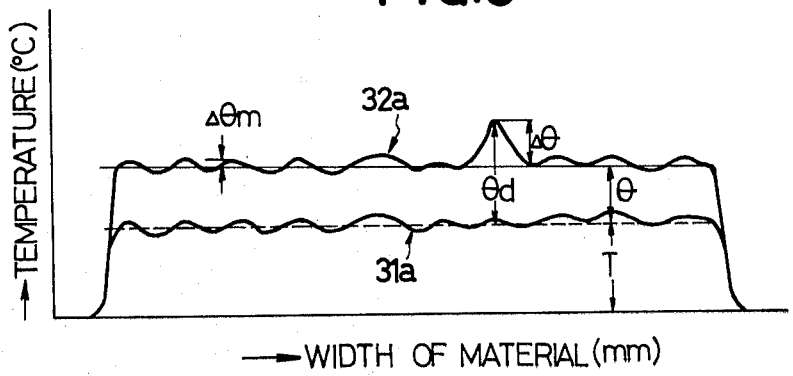
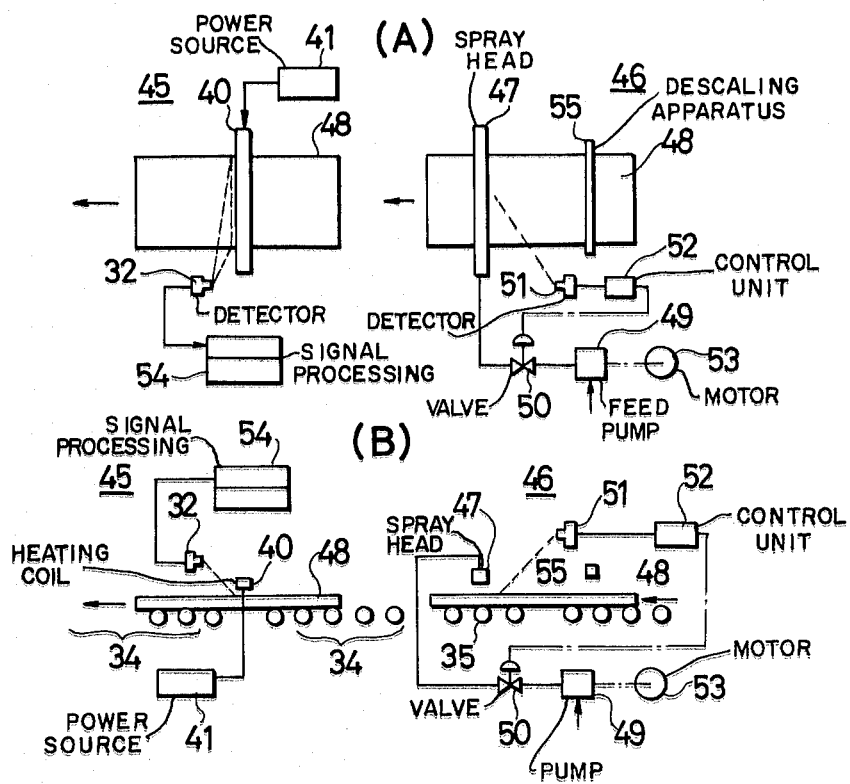

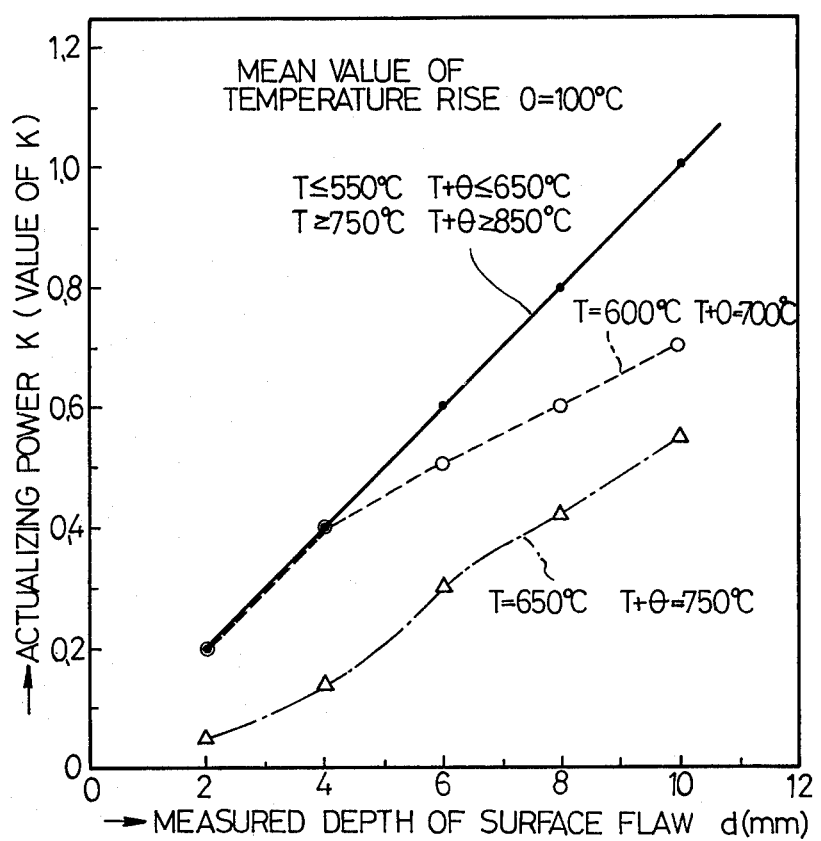

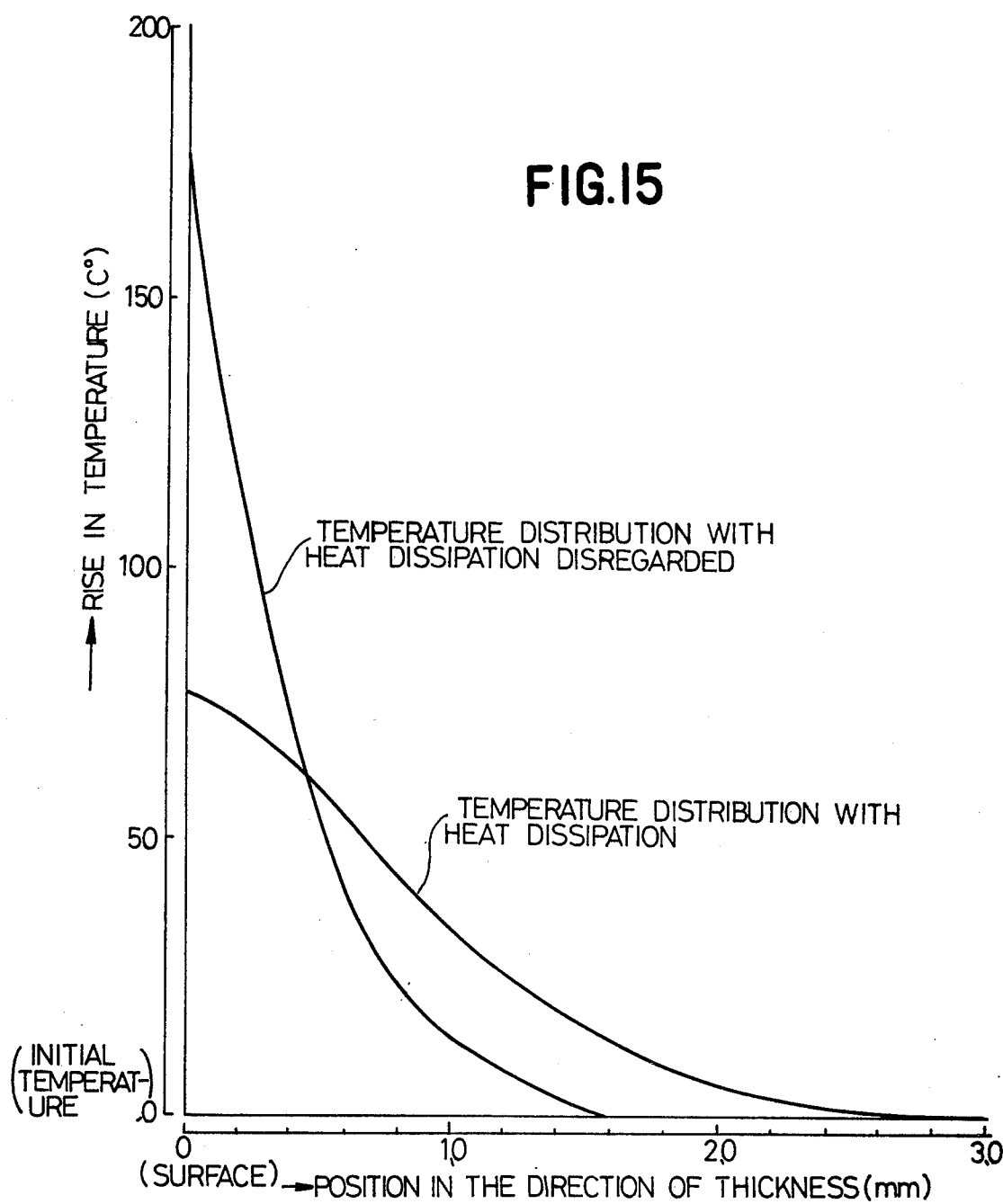

METHOD OF DETECTING A SURFACE FLAW OF METALLIC MATERIAL

BACKGROUND OF THE INVENTION

The present invention relates to a method of detecting a surface defect or flaw of metallic material, and specifically a method of detecting designed to carry out high precision detection of the depth of a surface defect or flaw of metallic material at any temperature.

Generally, various sorts of surface defects or flaws take shape in the manufacturing processes of metallic material. The surface flaws of these sorts are what must be detected and removed in a proper manner.

Given below will be a statement of surface flaws taking shape on iron and steel members constituting a sort of metallic material. In general practice, intermediate products of such iron and steel members as billets, blooms, slabs and the like are manufactured in the iron and steel manufacturing processes through a continuous casting process or a blooming or slabbing process. These intermediate products of iron and steel members have various shapes and various depths of surface flaws caused during in the course of the manufacturing processes.

In the conventional practice, each one of the above-mentioned iron and steel members manufactured by either a continuously casting apparatus or a blooming apparatus is subjected to cooling down to the normal temperature level, and then an inspection of whether or not surface flaws are present is conducted. Surface flaws, if any, are removed, and reheating is conducted, then the iron or steel member is properly rolled into a finished product, such as a steel plate, a hoop, a strip steel member, or the like.

The said intermediate products of iron and steel members of the normal temperature level have surface flaws removed by such means as melting and/or grinding, when the surface flaws are detected directly through visual inspection by an inspecting worker or when information with regard to the presence and the position of the flaws is given by such a surface flaw detection system as detects the presence of surface flaws of the iron and steel members and the positions of the surface flaws of the iron and steel members. However, the visual inspection by an inspecting worker has proved that measurement of the depth of a flaw is not practicable, and mere location of the presence of a flaw has been conducted. Even the said surface flaw detection system could only obtain information with regard to the presence and the position of the flaw, and it was not possible to obtain information with regard to the depth of the flaw. For this reason, in the flaw removal processes of scarfing and grinding, surface flaws have been removed in a manner of repeating the trial-and-error method wherein a melting workman and a grinding workman conducted scarfing and grinding to such depth and over such an area as were regarded intuitively by them to be appropriate. The scarfing workman and the grinding then workman conducted inspection once again thereafter with regard to whether or not the flaws had been removed. If some flaws remain untreated, the scarfing and grinding processes were repeated. On the other hand, in the case of introducing an apparatus for automatically removing surface flaws and combining the same with the above-mentioned surface flaw detection system, it cannot be helped but to statistically find in advance the maximum depth of flaws created, and to remove all of the detected surface flaws by as much as to the said maximum depth by the application of automatic scarfing and grinding processes. In this case, melting and grinding are often conducted to unrequired depth, to thus result in a gross metal loss. Besides, in the case of conducting removal a surface flaws in a manner of repeating the trial-and-error method for the purpose of reducing the said metal loss, considerable impairment of efficiency entails, which makes it imperative to increase the manhours for treatment of the flaws and the number of automatic flaw removal apparatuses as well, thus resulting in an increase in labor cost and equipment cost.

SUMMARY OF THE INVENTION

An object of the present invention is to provide a method of detecting a surface flaw of metallic material, featuring that the said problematical points are properly removed by detecting the depth of the surface flaw, so that the flaw is enabled to be removed at the minimum level of metal loss and efficiently enough, and tht a considerable economic effect can be achieved.

Another object of the present invention is as set forth below. The recent trend characterized by a few methods specifically designed for saving energy is such that iron and steel members manufactured by the application of a continuous casting process or a blooming process are charged in place into a heating oven while the iron and steel member are still hot enough, without cooling the same down to the normal temperature level or the vicinity thereof. This saves the fuel cost required for the heating oven and improves the capacity of the heating oven. This method is called an iron/steel member hot charge method). There is also a method wherein iron and steel members manufactured by the application of the said continuous casting process or the said blooming process are subjected to hot rolling, without being subjected to reheating at all, to also attain saving of energy. This method is called an iron/steel member direct rolling method. For the application of the iron/steel hot charge method and the iron/steel member direct rolling method, it is imperative that surface flaws of the iron/steel members be properly detected in an intermediate process between either the continuous casting process or the blooming process and the said heating oven process or the said hot rolling process, and that the surface flaws thus detected be removed in a proper manner. In the execution of the said hot charging and the said direct rolling, the said surface flaw detection system is arranged in place in the intermediate process between either the continuous casting process or the blooming process and the product rolling process. A difference between an intermediate product manufacturing plant and a finished product rolling plant is defined in terms of the capacity thereof, and depends upon such conditions of manufacture as the classification of steel and the sizes of products. Furthermore, the surface temperature of the iron/steel members, as the material for the intermediate products to be subjected to treatment by a hot surface flaw detecting means, is subjected to dispersion within a wide range of the normal temperature levels through approximately 1,200° C, according to such unexpected troubles as various irregularities that take shape in respective processes.

Therefore, in order to achieve not only the effect of energy saving but also the improvement of the yield through the reduction in metal loss, it is necessary that the surface flaw detecting means for such iron/steel members as the material for intermediate products set forth in the preceding paragraph be capable of detecting the depth of the surface flaws, as well as detecting the presence of the surface flaws, irrespective of the surface temperature of the iron/steel members.

To meet the above-mentioned requirement, still another other object of the present invention is to provide a method of detecting the surface flaws of the iron/steel members, that is well capable of detecting the depth of the surface flaws, irrespective of the level of the surface temperature of the iron/steel members.

BRIEF DESCRIPTION OF THE DRAWINGS

FIG. 8 is a diagram to show the output signals of a scanning type radiation dosimeter;

FIGS. 11, 12 are diagrams to show the relation between the actualizing function obtained at the slab surface temperature before induction heating at 100° C and 50° C in mean set value of temperature rise and the measured depth of a flaw;

FIG. 13 shows a series of the surface flaw detecting apparatuses for iron/steel members with such iron/steel members of 20° – 1,200° C as have strong magnetic properties;

FIG. 15 is a diagram of rising temperature in the direction of the thickness of the material under specific conditions;

DETAILED DESCRIPTION OF THE INVENTION:

A detailed description of the method of detection according to the present invention will be given below. To start with, in the subsequent paragraph there will e given a description of the principle of the detection of the position of a surface flaw, as well as that of the presence of the surface flaw.

Figures 6, 9:
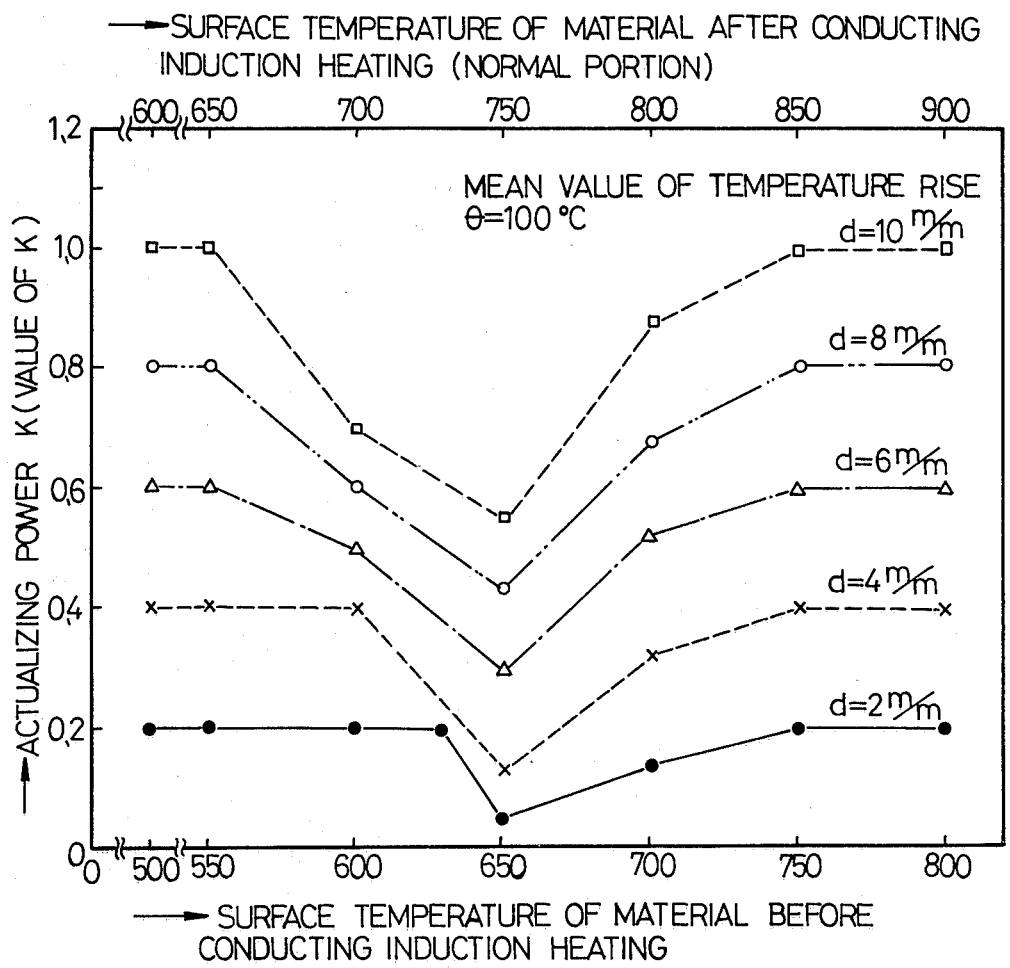
FIG. 6 is a diagram to show the types of such surface flaws as take shape on a continuously casting slab, the shapes of the said surface flaws, and the results of visual observation at the slab surface temprature of 600° C or over after induction heating.
FIGS. 9, 10 are digrams to show respectively the relation between the slab surface temperature before induction heating at 100° C and 50° C in mean set value of temperature rise and the actualizing function of the surface flaw.

When an induction current is caused to run through the surface layer to approximately the same depth as a flaw present on the metallic material by using an induction heating coil, or when the said surface layer is directly subjected to electrification, the surface of the metallic material is subjected to heating by the thermal action of the electric current. In this case, the flaw-bearing portion grows higher in temperature than other normal portions. FIG. 6, for example shows the types of such surface flaws as take shape on the iron/steel metallic material for an intermediate product. The figure shows, on a continuously casting slab, the shapes of the surface flaws, and the results of visual inspection at 600° C or over in surface temperature of the slab after being subjected to induction heating. In FIG. 6 "Crack-small" represents a case wherein a slight hot spot is observed in the peripheral area of the flaw, "Crack-large" represents a case wherein a considerable hot spot is observed in the peripheral area of the flaw, "Crack - hexagonal type" represents a case wherein a fairly remarkable hot spot is observed in the peripheral area of the flaw, "Oscillation crack" represents a case wherein high temperature is observed in a linear shape and considerable hot spots are overlapped, and "Blow hole crack" represents a case wherein the flow as a whole becomes high in temperature (hot surface). Therefore, when the said portion whereof the temperature rises high is taken as a surface flaw-bearing portion, and the said portion whereof the temperature rises high is subjected to detection by the employment of a thermometer, including an infrared ray thermometer or the like, which scans in the direction of the width of the metallic material along the induction heating coil, the position of the flaw can be detected from the position of the portion whereof the temperature has risen high in the scanning range.

The inventor investigated the point where the surface flaw-bearing portion is raised in terms of temperature by induction heating, and examined the machanism whereby the surface flaw-bearing portion is raised in terms of the temperature thereof. To put it in specific terms, when an induction current is caused to run through the surface layer of such a sort of metallic material as bears a surface flaw (hereinafter referred to as a flaw in a simplified term), by the employment of an induction heating coil, the low of the electric current along the induction heating coil is inhibited in the flaw-bearing portion, and a turbulence zone of the electric current is produced in the said flaw-bearing portion.

The electric current thus inhibited in the flaw-bearing portion is shunted to the lower portion (in the direction of the depth) of the flaw, and to the both ends of the flaw as well, in a manner conforming with the electrical resistance of the paths of the respective electric currents. At this time, the electric current thus shunted runs through such a shunt path or by-pass as has the minimum electrical resistance. To put it otherwise, the electric current shunted to the lower portion of the flaw is concentrated at the lower end in the direction of the depth of the flaw, and the electric current shunted to the both ends of the flaw runs in a manner of being concentrated at the end of the flaw. The quantity of the electric current thus subjected to shunt to the ends of the flaw is related to the depth and the length of the surface flaw.

In case a slight flaw present in the width of an opening is observed in a planar direction, the both ends of the flaw are higher in terms of current density than a flawless portion (hereinafter referred to as a normal portion) in the induction current path.

The surface portion of the material is heated by virtue of the thermal action of the induction current, and the temperature is further raised, in excess of the normal portion, at the both ends of the flaw where the current density has been raised to a higher level. With respect to a flow large enough in terms of the width of the opening thereof, the bottom portion of the flaw is also observable in a plane view, and the lower portion (the bottom) of the flaw, in addition to the both ends of the said flaw, likewise has the temperature raised by the concentration of the electric current.

Figure 1:
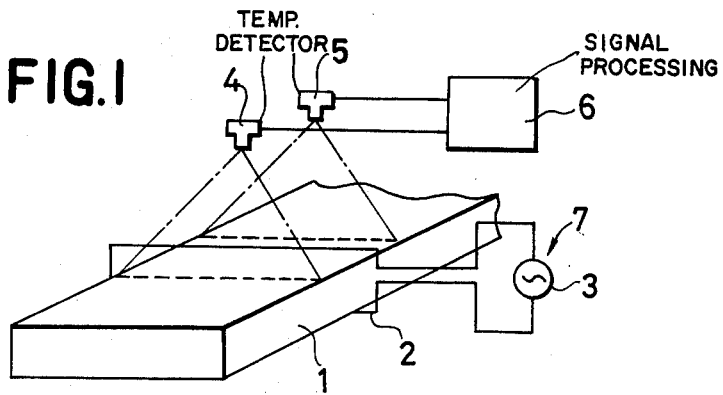
FIG. 1 is a diagram to show the method of detecting a surface flaw introduced in the present invention.

In the method of detecting a surface flaw, wherein a continuous linear induction current is produced in the vicinity of the surface of metallic material 1 by means such as a high-frequency induction heating apparatus 7 as comprises an induction heating coil 2 and a high-frequency power source 3, the surface layer thereof is subjected to induction heating, and, immediately after the induction heating, distribution of surface temperature is detected by the employment of a temperature distribution detector 4. Additionally, the state of temperature distribution before the induction heating is found in advance by the employment of another temperature distribution detector 5 and a signal processing apparatus. Then, whether or not a surface flaw is present is detected from deviation signals between the detecting signals of the said both detectors 4, 5, in such a manner as is shown in FIG. 1. The inventor examined the possibility of detecting the depth of the surface flaw in various ways, as set forth in the preceding paragraphs, and conducted a series of experiments on the basis of the said examination, which resulted in finding that a certain interrelation was present between the depth of the surface flaw and such values of temperature rise as are shown in FIGS. 2 and 3, which shows an example of the results of the said experiments.

Figure 2:
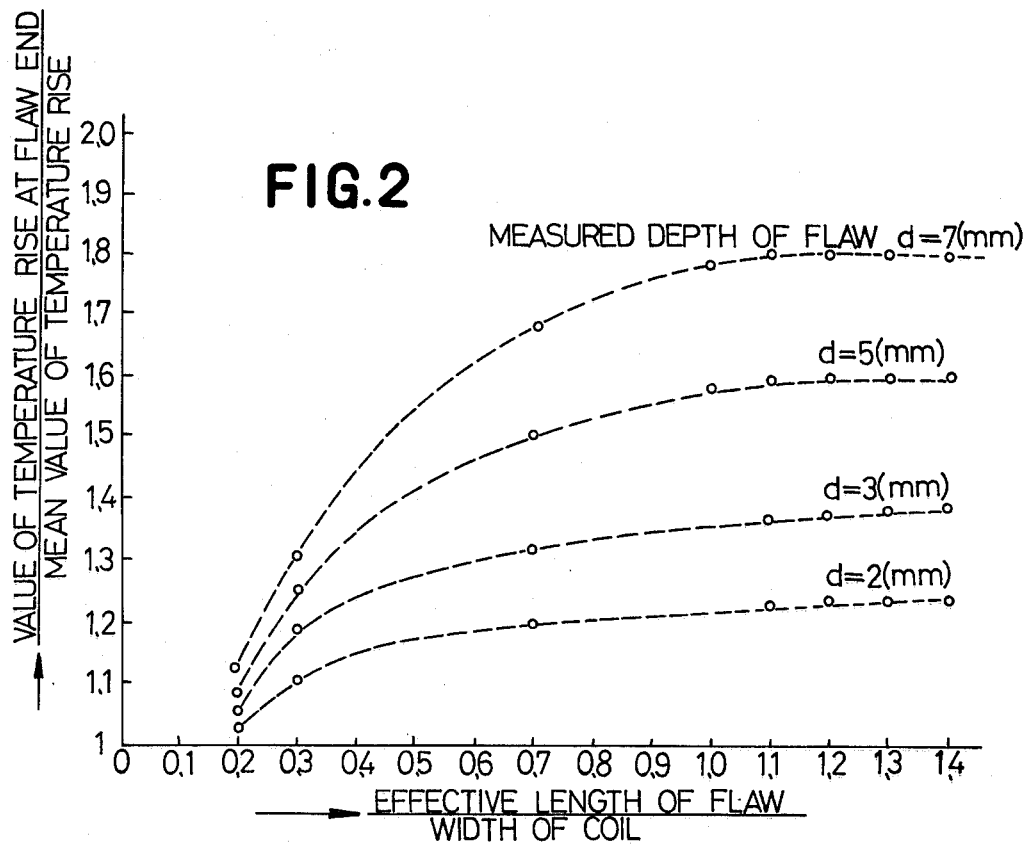
FIGS. 2, 3 are diagrams to show the interrelation between the depth of surface flaws and the values of rise in temperature.
Figure 3:
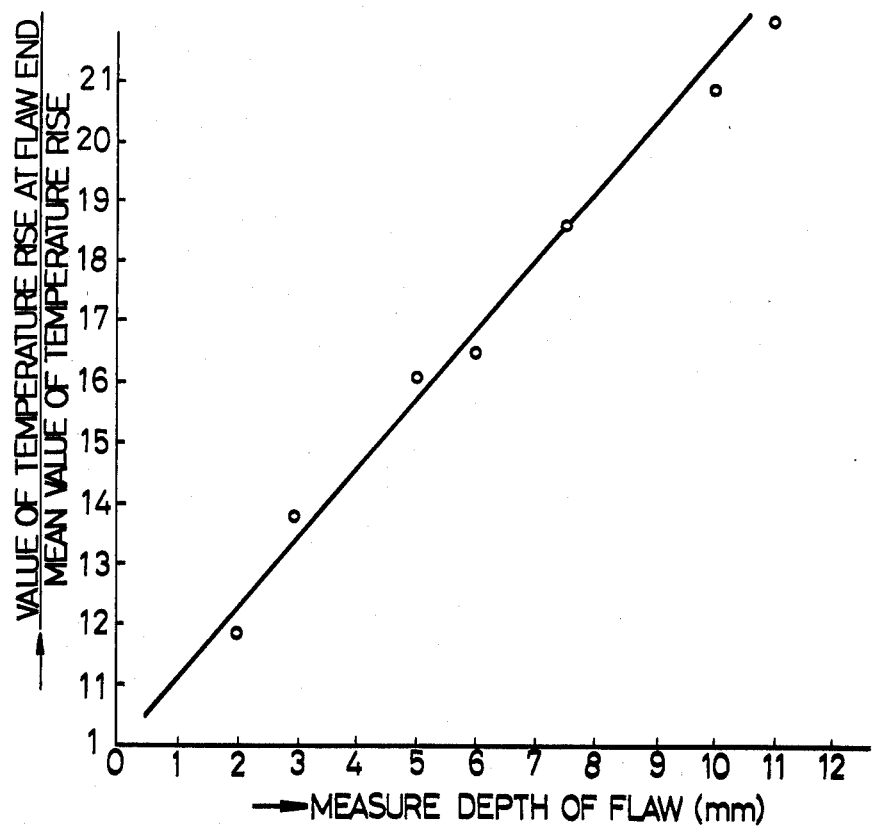

Shown in FIG. 2 is an arrangement of such test data as were obtained as the results of a series of tests conducted in a repeated manner by such apparatus and such test conditions as are shown in FIG. 1 and Table 1, respectively, and FIG. 2 reveals the relation between with measured depth of the flaw specifically taken as a parameter. Herein, the effective length of the flaw represents the length of the orthogonal constituents of the surface flaw to the coil; the width of the coil represents the length of the coil in the longitudinal direction of the material, and the mean value of temperature rise represents the difference in temperature distribution between that before induction heating and that after induction heating, to put it otherwise, a mean value of deviations of temperature distribution.

Table 1

| Induction heating apparatus 7 | | |
| --- | --- | --- |
| 1. Frequency | | 30KHz, constant |
| 2. Dimensions of induction heating coil Inner size in the direction of | | |
| the thickness of material under test | | 75 [mm] |
| Inner size in the direction of the width of material under test | | 110 [mm] |
| Size in the direction of the length of material under test | | 10 [mm] |
| Material under test 1 | | |
| 1. Material | Such a continuously cast slab piece as makes it impossible to observe the presence of a surface flaw by visual observation from the surface | |
| 2. Dimensions | Thickness | 50 (mm) |
| | Width | 90 (mm) |
| | Length (in the direction of the material) | 200 (mm) |
| 3. Speed of transfer | | 10 [mm/sec] |
| 4. Temperature | Initial temperature (temperature before induction heating) | 550 [° C] |
| | Mean temperature after heating | 650 [° C] |
| Temperature distribution detectors 4, 5 | | |
| 1. Detectors | Of the linear scanning type; provided with built-in infrared ray thermometer of 0.5 [° C] in sensitivity at 700 [° C] in temperature of substance to be measured | |
| 2. Position of scanning of material under test by detector 4 | | |
| | Linear scanning of surface under coil edge in the direction of transfer of material under test | |
| Method of measurement of depth of surface flaw | | |
| | The depth of a surface flaw was found by subjecting the material under test at every 1 mm thereof in the direction of its thickness. | |

As clarified through FIG. 2, [the value of temperature rise at the end of the surface flaw/the mean value of temperature rise] becomes virtually constant in the range of [the effective length of the flaw/the width of the coil] $\geq 1$, and the larger in value the measured depth of the flaw is, the larger [the value of temperature rise at the end of the surface flaw/the means value of temperature rise] becomes. To put it otherwise, in case the effective length of the flaw is longer than the width of the induction current path (the width of the induction heating coil), the temperature at the end of the surface flaw is related virtually only to the depth of the flaw.

Shown in FIG. 3 is a plot of the data of the surface flaw given as [measured depth of the flaw] wherein [the effective length of the flaw/the width of the coil] $\geq 1$, and the data of [the value of temperature rise at the end of the surface flaw/the mean value of temperature rise].

FIG. 3 reveals that [the value of temperature rise at the end of the surface flaw/the mean value of temperature rise] and the depth of the flaw are virtually proportionate to each other.

To put it otherwise, when the points shown in FIG. 3 and Table 1 are taken as criteria, the depth of the surface flaw $d$ [mm] can be expressed by the formula of $$d = K_1 \cdot (\frac{T}{Tm} - K_2) \tag{1}$$

Here, $K_1$ is approximately 8.7, and $K_2$ is 1. Tm represents the mean value of temperature rise, and T represents the value of temperature rise at the end of the surface flaw. This reveals that, in case the length of the flaw is larger in value than the width of the electric current path (the width of the induction heating coil) among others, the value of the temperature rise at the end of the surface flaw is related virtually only to the depth of the flaw. As to the surface flaw to be expressed by [the effective length of the flaw/the width of the coil] $< 1$ shown in FIG. 2, the value of the temperature rise at the end of the surface flaw can be made proportionate virtually to the depth of the flaw by rendering the electric current path only minute in terms of the width thereof in a reverse manner. Therefore, the depth of the flaw can be found by taking the level of the value of temperature rise of the material as a criterion therefor.

Now, the present invention is specifically designed for measuring the depth of the surface flaw on the basis of such a consideration as is set forth above and a knowledge obtained through a series of experiments. The subject matter thereof is carried out in that some metallic material is subjected to the continuous transfer at constant speed in an induction heating coil or along the said coil. Alternately the induction heating coil is subjected to continuous transfer at constant speed along some static metallic material in a reverse manner. A high-frequency linear induction current is thereby caused to be generated in the said metallic material, whereby the temperature of the surface layer of the said material in the coil projection portion is caused to rise in a squential manner. Such non-uniformity of temperature as is produced in the portion bearing a surface flaw is detected, to thus carry out detection of the surface flaw. The depth of the surface flaw is found in a proper manner by taking the degree of the said non-uniformity of temperature as a guide criterion therefor.

Figure 4:
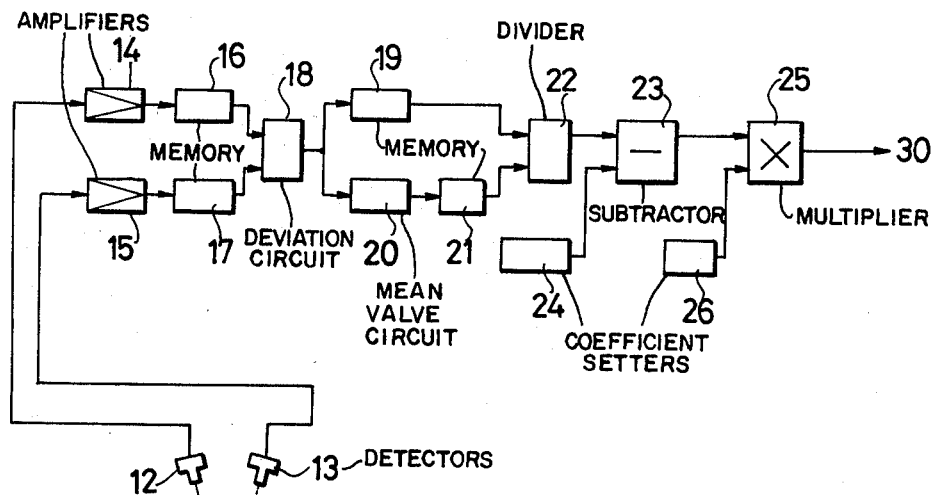
FIG. 4 is a flow chart to show an example of the constitution of the surface flaw detecting apparatus to be employed in the case of applying the present invention to a continuously casting slab.

A description of the method of detecting a surface flaw introduced in the present invention will be given below by making reference to an illustration wherein the said method is applied to a continuously casting slab, as shown in FIG. 4. Reference 8 is a table roller to be rotated at constant speed; 9 is a continuously casting slab to be transferred at constant speed by the table roller 8; 10 is a roll of high-frequency induction heating coil arranged in place between the table rollers in such a manner that the slab can be placed through the said coil; 11 is a high-frequency power source for the said coil 10; 12 is a temperature distribution detector that is arranged in place on the input side of the said coil 10, and scans the surface of the slab 9 before its being heated by scanning in the direction of the width thereof, and detects distribution of temperature in a sequential manner; and 13 is a temperature distribution detector that is arranged on the output side of the said coil 10 and detects the temperature distribution in the direction of the width thereof immediately after linear induction heating.

Now, with regard to the induction heating coil 10, there is preferably used a type of coil whereof the width is small-dimensioned and an induction current of a minute width can be produced. With regard to a surface flaw in the direction of casting the said slab 9, for instance an oscillation crack, it is likewise recommended that the slab 9 be arranged in such a manner as to be inclined by an appropriate angle in the direction making a right angle with said direction of casting, for the purpose of obtaining sufficient effective length of the surface flaw.

Reference 14, 15 are amplifiers designed for amplifying temperature distribution signals transmitted from the said detectors 12, 13, respectively. Reference 16, 17 are such memory reproducers as keep the temperature distribution signals in memory temporarily in a sequential manner, and transmit the temperature distribution signals likewise in a sequential manner by delaying the detecting signal before heating either of such a length of time as is required for transferring a steel member of the distance between the positions for observing the said detectors 12, 13, or by an amount dependent on the frequencies of scanning within the said length of time. Reference 18 is a deviation operator that feeds as an output such a deviation signal as is corresponding to the value of temperature rise. Reference 19 is a memory reproducer that keeps a derivation signal in memory and reproduces the same. Reference 20 is a mean value operator that operates a mean value of temperature rise by taking a deviation signal as a criterion thereof. Reference 21 is a memory reproducer that keeps in memory and reproduces a mean value of temperature rise. Reference 22 is an operator that conducts operation of [the value of temperature rise/the mean value of temperature rise] for each and every time of scanning by the said detector. Reference 23 is a subtractor. Reference 24 is a coefficient setter. Reference 25 is a multiplier. Reference 26 is a coefficient setter.

Figure 5:
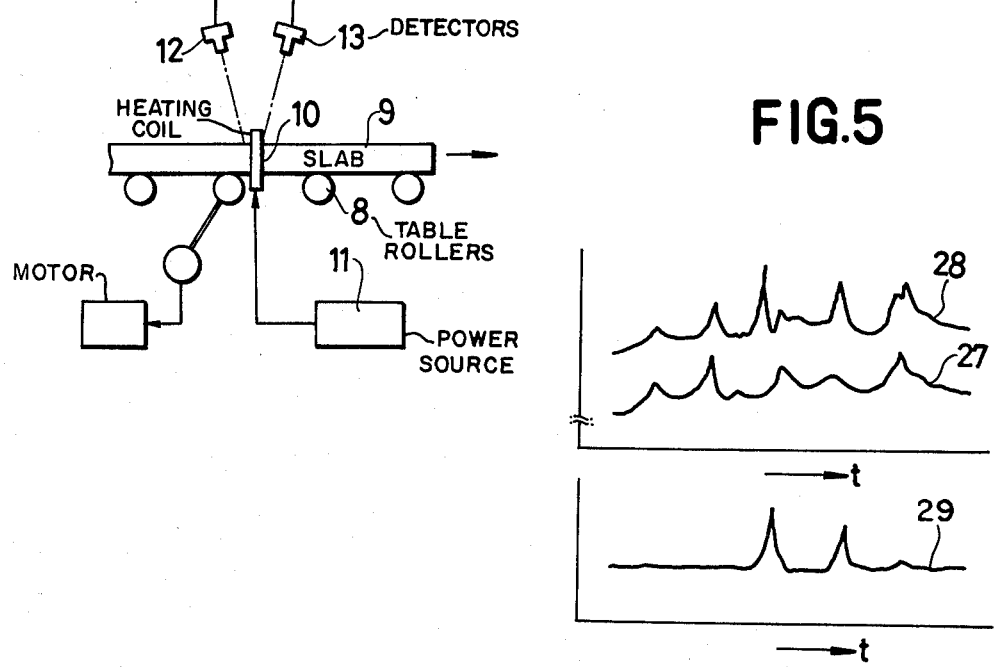
FIG. 5 is a diagram to show examples of output signals of a memory reproducer and a deviation operator during one scanning period by a temperature distribution detector.

Shown in FIG. 5 are exemplified output signals 27, 28, 29 of the memory reproducer 16, 17 and the deviation operator 18 at one and the same time.

In the case of the surface flaw detecting apparatus constituted in such a manner as set forth in the preceding paragraphs, only the surface layer of the slab of the coil projecting portion is subjected to high-frequency induction heating in a sequential manner, in the course of continuous transfer, at constant speed, of the slab 9. The temperature of the slab 9 before its being heated and the temperature of the slab 9 immediately after its being heated are measured by the detectors 12, 13, and the temperature thus measured are kept in memory in the memory reproducers 16, 17 in a sequential manner. The memory reproducer 16 reproduces and transmits necessary signals corresponding to the results of measurement of the temperature before heaing either for such a length of time as is required for transferring the slab 9 over the observation distance of the surface of the slab 9 for the reproduction output of the memory reproducer 17, or by staggering the results of meaurement of the temperature before heating by as often as the frequencies of scanning within the said length of time. The difference between the detecting signals for respective times of scanning is provided by the deviation operator 18, and the value of the temperature rise on the surface of the slab 9 is thus found.

However, in case the temperature of the slab before heating is uniform over the whole surface, measurement of the temperature by scanning is not required. In this case measurement of the temperature at one typical spot is sufficient. To put it otherwise, operation of the deviation can be conducted simply enough by merely subtracting some certain value (the value of the temperature measured at the said typical spot) from the result of the measurement of the temperature conducted by the detector 13 arranged on the side of the output.

The said deviation signal is kept in memory in the memory reproducer 19 and the mean value operator 20 determines the mean value of temperature rise, as well as the deviation signal, and causes the results of the operation to be kept in memory in the memory reproducer 21.

The reproducers 19, 21 the value of temperature rise and the mean value of temperature rise for each and every case of scanning. The division operator 22 finds a proportion of the value of temperature rise to the mean value of temperature rise (the value of temperature rise/the mean value of temperature rise). The subtractor 23 carries out substraction of such a coefficient 1 as is set in the coefficient setter 24 from [the value of temperature rise/the mean value of temperature rise]. The multiplier 25 carries out multiplication of [(the value of temperature rise/the mean value of temperature rise)-1] by such a coefficient (8.7) as is set in the coefficient setter 26. A signal 30 designating the depth of a flaw is thus generated as an output. The signal thus generated is subjected to a-c/d-c conversion, and is displayed on a line printer, a cathode-ray tube, and/or the like. It goes without saying that a part or the whole of the said signal processing portion can be subjected to proper processing by a computer for information processing.

Additionally, it goes without saying that the position of a surface flaw on the surface of the slab can be detected by selecting the speed of transfer of a steel member, the frequency of scanning and the speed of scanning by the temperature distribution detector as the guide criteria therefor.

The gist of the description given in the preceding paragraphs lies in that a continuous linear induction current is so caused as to be provided on the surface layer of a metallic material by the employment of a high-frequency induction heating apparatus. The difference in the heat release value attributable to the difference in electrical resistance or in degree of electrical current concentration between a surface flaw and a normal surface portion in a continuous linear induction current path is properly detected by the employment of a temperature distribution detector immediately after induction heating, the surface region before conduction induction heating and the corresponding surface region of material immediately after conducting heating are detectected by said temperature distribution detectors. Deviation signals for the detecting signals generated by the detectors is properly found, and a signal for a mean value of temperature rise is formed by taking the said deviation signal as a criterion. Then the depth of a surface flaw is found by taking the ratio of the said deviation signals to the signal for a mean value of temperature rise as a criterion therefor. To put it otherwise, now that distribution of temperature of the material before and after induction heating is properly detected and the depth of a flaw is found by taking the deviation of temperature distribution as a criterion therefor, the depth of the flaw can be properly found in a satisfactory manner, even in case non-uniformity of temperature is present on the surface of the material before conducting induction heating.

While coming up with the above-mentioned method, the inventor examined a method of detecting the depth of a surface flaw by the application of a process of detecting distribution of surface temperature immediately after conducting induction heating.

In the description given above, the mean value of the difference in temperature distribution in the directon of a current path, before and after induction heating, and in the induction current path, is defined to the mean value of temperature rise. The said mean value of temperature rise provide a marked difference depending upon whether or not a surface flaw is present on the said current path.

With regard to the value of temperature rise in the normal portion of the material by means of induction heating, the said value of temperature rise can be found by conducting proper operation of required power by taking the dimensions of a coil, the dimensions of the material, the speed of material feed, and the said value of temperature rise in the normal portion of the material as the criteria therefor. By setting the feed rate and the power in such a manner as to enable the said predetermined value of temperature rise to be obtained in a proper manner. The set value $\theta$ of temperature rise and the aforementioned mean value T of temperature rise may be so regarded as to be virtually equal, since the area of a surface flaw present in an electrical current path is only quite small, compared with the area of the normal portion. Accordingly, the value of temperature rise set in such a manner as is described in the preceding paragraphs may be defined to be a mean set value $\theta$ of temperature rise. Furthermore, when the hot spot temperature to be generated in the portion of a flaw by induction heating is expressed to be $\theta d$, the experimental formula of (1) given above can be modified as shown below.

$$d = 8.7 \left( \frac{T}{Tm} - 1 \right) \quad (2)$$
$$\approx 8.7 \left( \frac{\theta d}{\theta} - 1 \right)$$

Suppose that $\Delta\theta = \theta d - \theta$ $$d \alpha \frac{\Delta\theta}{\theta} \quad (3)$$

To put it otherwise, the depth d of the surface flaw is proportionate to the ratio of such hot spot temperature $\theta d$ as is generated in the portion of a surface flaw by induction heating to the mean set value $\theta$ of temperature rise.

The original and primary object of the induction heating to be applied in the case of such a method of detecting a surface flaw as employs an induction heating process does not always rest with raising the temperature of the metallic material by heating. The said object rests when that temperature difference is caused to be produced between the normal portion and the portion bearing a surface flaw in such an operating process wherein the surface portion of the metallic material is subjected to heating for raising the temperature thereof from some certain initial level of temperature up to some certain preset level of temperature. To put it otherwise, the said object rests when a surface flaw-bearing portion is actualized thermally as a portion wherein the temperature is raised up to a high enough level.

Therefore, when the mean set value of temperature rise by the application of an induction heating process is expressed to be $\theta$, and the temperature at such a hot spot as takes shape in a surface flaw-bearing portion is expressed to be $\theta d$, the thermally actualizing power K of the surface flaw-bearing portion by induction heating on the surface of metallic material, (the value of K), is to be defined to be what is expressed by the following formula.

$$K = \frac{\Delta\theta}{\theta} = \frac{\theta d - \theta}{\theta} = \frac{\theta d}{\theta} - 1 \quad (4)$$

When the surface portion of material is subjected to heating at such heating speed as can neglect diffusion of heat, then the surface temperature of the material is caused to rise virtually according to the distribution of electric current density, and the distribution of electric current density is determined by the size (including length and depth), the shape, and/or the like of a flaw. Then the said actualizing power K is what is inherent and determined by taking the size and the shape of a flaw. Therefore, once the surface flaw is thus determined, the temperature difference $\Delta\theta$ is proportionate to the mean set value of temperature rise $\theta$.

According to the results of a series of experiments conducted with such a continuously cast low-carbon steel slab as is described in a paragraph given later, the actualizing power K (the value of K) was determined by the primary function of the depth of a surface flaw $d$ under some certain condition. As to the surface flaw of $d = 1 - 10$mm in depth, and wherein the mean set value of temperature rise $\theta$ was 50° C. When the surface temperature T before induction heating of a slab was T $\leq$ 650° C, then T + $\theta$ 700° C. When T $\geq$ 750° C, then T + $\theta \geq$ 800° C. When the mean set value $\theta$ of temperature rise is 100° C, then with the surface temperature T before induction heating of a slab after T $\leq$ 550° C, then T + $\theta \leq$ 650° C. With T $\geq$ 750° C then T + $\theta \geq$ 850° C. In these tests, the relation between the depth $d$ of the surface flaw and the actualizing power K was $$K = d/10 \quad (5)$$

When the relation shown in the formula (5) is established, other conditions are as shown below.
Instantaneous field of view of radiation dosimeter 1mm × 2mm
Conditions of induction heating
Frequency 50 KHz
Heating rate 270° C/sec Now that the time required of the material to pass under the width of the coil is the heating time, and the material has the temperature raised by heating by as much as the mean value of temperature rise thereof in the course of time required for passage, the heating rate is defined in such a manner as is shown in the following formula.

$$\text{Heating rate [° C/sec]} = \frac{\text{Material transfer speed [mm/sec]}}{\text{Width of coil (Length of material in the direction of transfer [mm])}} \cdot \text{Means value of temperature rise}$$

Even in case the material is free from a surface flaw, the temperature thereof still has more or less non-uniformity even a radiation dosimeter of the line scanning type has more or less noise generated in the system thereof. The output side of the radiation dosimeter has more or less non-uniformity of temperature even in a flawless portion thereof. When the said non-uniformity of temperature (and the noise level as well) is expressed to be $\Delta\theta m$, and the said temperature difference $\Delta\theta$ is of the same level and has virtually the same frequency composition as the non-uniformity of temperature $\Delta\theta m$, it is difficult to discriminate $\Delta\theta$ from $\Delta\theta m$. To put it otherwise, it is nothing easy to conduct detection thereof as a surface flaw.

For discriminating the said $\Delta\theta$ as a flaw signal from the said noise leve $\Delta\theta m$, $\Delta\theta/\Delta\theta m$, i.e., S/N (flaw signal level/noise level) is required to be 1.5 - 2 or over.

The noise level $\Delta\theta m$ is determined by such noise composition as is characteristic of a radiation dosimeter of the linear scanning type, and by the level of the non-uniformity of temperature on the surface of the material in a flawless portion. The said factors to determine the noise level $\Delta\theta m$ has nothing to do with the mean set value of temperature rise $\theta$ by induction heating, and is virtually constant.

Therefore, in case the relation between various surface flaws and the thermal activating power K (value of K) of a surface flaw-bearing portion on the surface of the material, also the noise level $\Delta\theta m$, is known. As a result the minimum mean set value of temperature rise $\theta$min, required for detecting by the application of the said formula of S/N = 15 can be established, with regard to a flaw to be detected. To put it otherwise, the required flaw signal level $\Delta\theta$ can be determined by taking the noise level $\theta\Delta m$ and the S/N ratio as the criteria therefor, and the minimum mean set value of temperature rise $\theta$min can be determined by taking the value of K characteristic of a flaw to be detected as a criterion therefor.

It goes without saying that the mean value of temperature rise may be so set as to be in excess of the minimum mean set value of temperature rise $\theta$min. For all that, however, when the rate of processing the material [ton/hour] is the same, the capacity of the induction heating apparatus is virtually proportionate to the mean set value of temperature rise, and the equipment cost is thus virtually proportionate to the capacity of the equipment. An increase in the mean set value of temperature rise up to an extremely hig level makes it imperative to rise excessive equipment investments. Hence, it is far from being economical, although detection of surface flaws can be facilitated thereby.

On the part of the end of a surface flaw and/or the bottom of a surface flaw, created by the concentration of induction currents, the area of a high-temperature spot, that is to say, a so-called hot spot, is subjected to fluctuation, according to the size (length, depth) and the shape of the surface flaw.

Therefore, it is recommendable that the instantaneous field of view of a radiation dosimeter of the scanning type be so selected as to be virtually the same as the minimum dimensions of a hot spot taking shape on a surface flaw.

Furthermore, to enable diffusion of heat to be neglected, the higher the said heating rate at the time of obtaining the mean set value of temperature rise is, the more desirable.

As set forth above, the heat actualizing power (value of K) of a surface portion bearing a flaw attributable to induction heating is what is determined by the depth $d$ of the surface flaw. This occurs when the width of the induction current path is so selected as to be small enough, hence characteristic of a surface flaw, and the surface flaw signal level $\Delta\theta$ is increased in proportion to the mean set value of temperature rise $\theta$. Therefore, when a mean set value of temperature rise representing the minimum requirement is properly selected by taking the noise level $\Delta\theta m$, a proper S/N ratio required for discriminating the flaw signal level $\Delta\theta$ and the noise level $\Delta\theta m$ from each other, and the value of K representing the surface flaw of the minimum depth and required for detecting the depth of the surface flaw as guide criteria, induction heating is conducted by as much as the said minimum mean set value of temperature rise $\theta$min. The surface flaw-bearing portion is then actualized as a high-temperature portion by virtue of a difference between the surface flaw-bearing portion and the normal portion in terms of the concentration of the induction currents. Scanning and measurement of the temperature of the surface of the material are conducted immediately after heating, by the employment of a radiation dosimeter of the scanning type, whereby the depth of a surface flaw can be found by learning the level of the peak of an output signal to be generated by the said radiation dosimeter.

In case the metallic material to be subjected to detection is an iron or steel member, presence of a surface flaw and the depth thereof are required to be detected with high precision, as set forth above, irrespective that the surface temperature of the iron or steel member is of any level within the range of 20° – 1,200° C. In connection with this aspect, this applicant has acquired a knowledge that, when the surface temperature of an iron or steel member having especially strong magnetic properties, among multifarious iron and steel members of various surface temperature levels, is in the vicinity of the magnetic transformation point, the thermal actualizing power K (value of K) of the surface portion bearing a flaw attributable to induction heating, which is the value that ought to be determined by the depth $d$ of the surface flaw and hence characteristic of the surface flaw, is deteriorated, whereby precision of detecting the presence of a surface flaw and precision of finding the depth of the surface flaw as well are deteriorated.

To put it otherwise, in the case of an iron or steel member having ferro magnetic substance, the said member absorbs transformation latent heat at the level of the temperature of the magnetic transformation point or curie point. In case the temperature of the magnetic transformation point is in the range of such temperature as is raised by induction heating, includes such a hot spot as takes shape on a flaw-bearing portion. To put it otherwise, when the temperature is raised up to such a level as is in excess of the magnetic transformation point temperature, including a hot spot on a surface flaw-bearing portion, in the process of raising the temperature up to the level of a designated mean value of temperature rise, the said actualizing power K, or the value of K, comes to lose its proportion to the depth of the surface flaw. This occurs even in case the means value of temperature rise remains constant. As a result the precision of finding the depth of the surface flaw by the level of the value of the temperature rise of a high-temperature portion is deteriorated. similarly, deteriorated is the precision of detecting the presence of the surface flaw.

Given below will be a detailed description with regard to the aspect that, when temperature is raised in the process of raising the temperature up to the level of a designated mean value of temperature rise, in such a manner that the high-temperature portion of the surface bearing a flaw exceeds the magnetic transformation point in terms of temperature, the actualizing power K comes to lose its proportion to the depth of the surface flaw, even in case the mean value of temperature rise remains constant.

Figure 7:
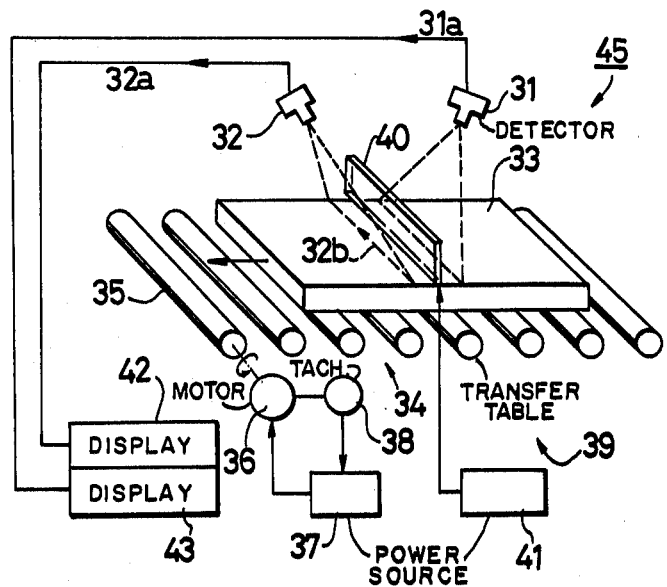
FIG. 7 is a perspective to show another example of the constitution of the surface flaw detecting apparatus for materializing the method introduced in the present invention.

Shown in FIG. 7 is a perspective of an exemplified constitution of a surface flaw detecting apparatus wherefor the present invention is put to working.

In FIG. 7, 34 is a material transfer apparatus, which comprises a plurality of table rollers 35, a driving motor 36 for rotating the said table rollers 35, a power source 37 for the said motor 36, and a tachometer 38. The plurality of table rollers 35 are so designed as to be of the interlocking system, not specifically shown as they are. 39 is an induction heater, which comprises one roll of induction heating coil (transverse flux heating coil) 40 and a high-frequency power source 41 for the said coil 40. An iron or steel member 33 is transferred at constant speed by the said transfer apparatus 34, passes under the said induction heating coil 40, and the top surface portion of the iron or steel member transferred along the said heating coil 40 is subjected to heating by as much as a designated mean set value of temperature rise in a sequential manner, thus having the temperature thereof raised in a proper manner. Reference 32, as well as 31, is a radiation dosimeter of the scanning type, provided with an optical scanning system and a light-to-electricity conversion system. Line scanning of the surface of an iron or steel member 33 is carried out on the input side and the output side of the induction heating coil 40 in the direction of the width of the said surface over a specified area of instantaneous field of view. Output signals such an electrical signal are generated corresponding to an instantaneous power. Reference 42, as well as 43, is a cathode-ray tube for displaying an output signal generated by the said radiation dosimeter 32, as well as 31, respectively.

FIG. 8 is such a drawing which shows on a temperature scale the output signals 31a, 32a of the radiation dosimeters 31, 32, measured at the time of conducting one time of scanning, before and immediately after induction heating, in the direction of the width of an iron or steel member 33, at the same position in the direction of transfer of the said iron or steel member 33, by the employment of the said radiation dosimeters 31, 32 shown in FIG. 7. FIG. 8, $T_1$ represents the surface temperature of the material before conducting induction heating, $\theta$ represents the mean set value of temperature rise attributable to induction heating, $\theta d$ represents the value of the raised high temperature of the surface flaw-bearing portion, the $\Delta\theta$ represents the value of the difference between the mean set value of temperature rise $\theta$ and the said value of the raised high temperature of the surface flaw-bearing portion $\theta d$. The said value of the difference $\Delta\theta$ makes a peak signal, that is a flaw signal, in the output signal on the radiation dosimeter 32. $\Delta\theta m$ represents the noise level in the output signal on the radiation dosimeter 32 and comprises slight non-uniformity of temperature in a flawless portion of the material subjected to either hot working or cold working and such a noise as is generated out of the system of the radiation dosimeter 32.

The applicant sought to find the relation between the surface temperature of a continuously cast slab of low carbon steel of 750° C in magnetic transformation point temperature Tc and the actualizing power of a surface flaw, before conducting induction heating, by specifically selecting as parameters the mean set value of temperature rise $\theta$ and multifarious surface flaws of various levels of depth (multifarious levels of actualizing power K).

Figure 10:
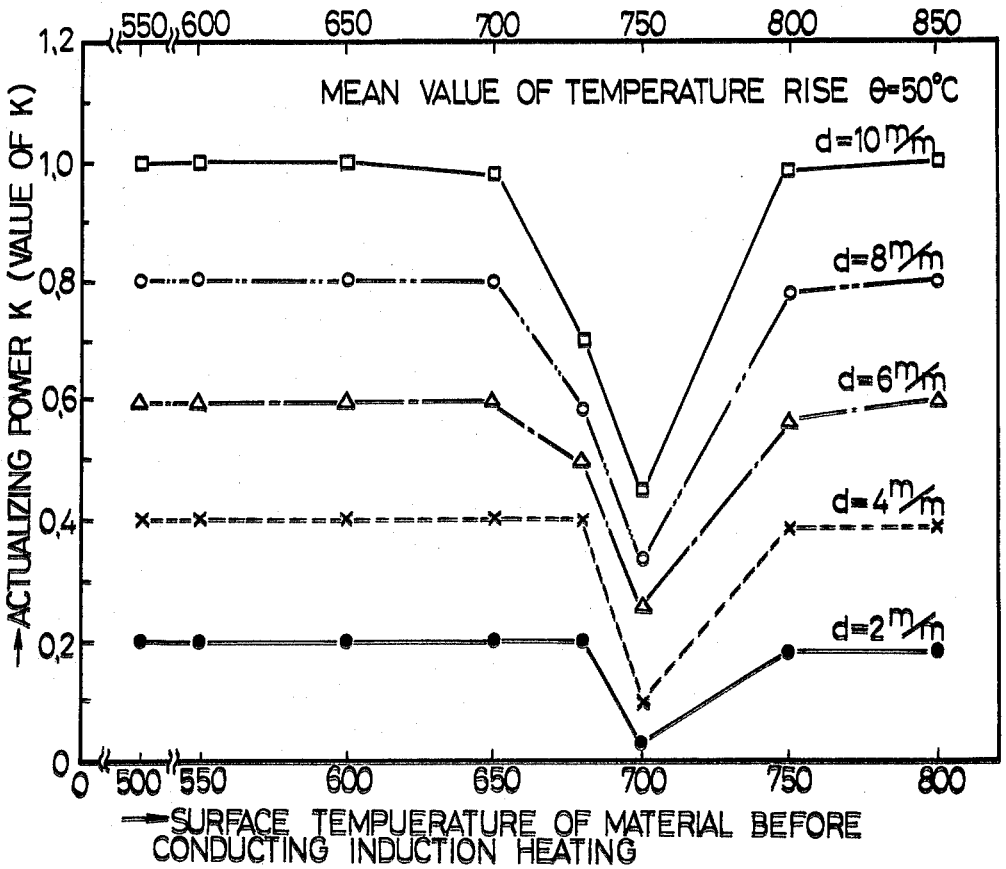

The results of this attempt are as shown in FIG. 9 and FIG. 10, of which FIG. 9 shows the results obtained in case the mean value of temperature rise $\theta$ was 100° C, and FIG. 10 shows the results obtained in case the mean value of temperature rise $\theta$ was 50° C. By the way, the depth of the flaw $d$ given in the said drawings represents such a value as was measured by the application of such a method as is described below. The area of the instantaneous field of view of the radiation dosimeter of the scanning type 32 was 1mm × 2mm, and the frequency for induction heating was 50 KHz.

Figure 12:
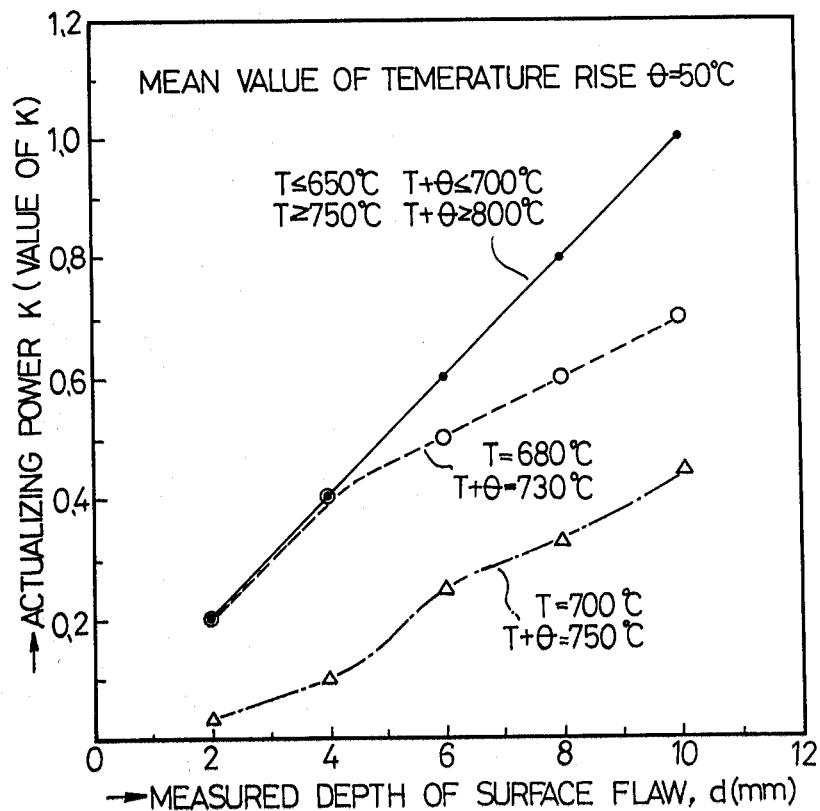

The relation between the measured depth of the surface flaw found by the application of a method of turning by steps on such a surface flaw-bearing portion of the said slab which was detected as a high-temperature portion (a method of measurement of the depth of a surface flaw, to be conducted by turning the surface by as much as every 1mm) and such a value of K as was found by taking the said surface temperature of the slab before conducting induction heating, is shown in FIG. 11 and FIG. 12. Shown in FIG. 11 is the relation in case the mean value of temperature rise $\theta$ was 100° C, and shown in FIG. 12 is the relation in case the mean value of temperature rise $\theta$ was 50° C, respectively.

FIGS. 11 and 12 reveal that, in case the high-temperature portion of the normal portion of the slab and that on the surface flaw-bearing portion of the slab are not in excess of 750° C in magnetic transformation point temperature Tc, then in the process of temperature rise by as much as the designated mean set value of temperature rise $\theta$, at the time of conducting induction heating by as much as the said mean value of temperature rise, the depth $d$ of the surface flaw is proportionate to the actualizing power K (value of K). To put it otherwise, FIGS. 11 and 12 reveal that the depth $d$ of the surface flaw is proportionate to the peak level of the output signal on the radiation dosimeter 32.

In case the temperature of the slab before conducting induction heating is in the vicinity of the temperature of the magnetic transformation point, and the high-temperature point taking shape on the flaw-bearing portion in the process of induction heating is in excess of the magnetic transformation point in terms of temperature, as shown in FIGS. 9 through 12, then the surface temperature of the slab before conducting induction heating becomes $T_1$(°C), the mean set value becomes $\theta$(°C), and the temperature at such a high temperature point as is detected at the flaw-bearing portion becomes ($\theta + \Delta\theta$)(°C), respectively. The actualizing power K (value of K) is then as shown by the following formula (4), $$K = \frac{\Delta\theta}{\theta}, \qquad (4)$$

Therefore, the temperature of the hot spot found on the flaw-bearing portion becomes as is shown in the following formula.
$$T_1 + \theta + \Delta\theta = T_1 + (1+K)\theta \ldots \qquad (5)$$

Therefore, in case the said surface temperature $T_1$ meets the requirement of the following formula, $$T_1 < Tc \ldots \qquad (6)$$

and, in case the said temperature of the hot spot $T_1 + (1+K)\theta$ meets the requirement of the following formula (7), $$T_1 + (1+K)\theta > Tc \ldots \qquad (7)$$

the temperature of the hot spot on the flaw-bearing portion is kept free from rising until transformation is completed, or until the material has absorbed the latent heat by transformation, and the temperature rises again when the transformation is completed. Therefore, when the temperature is raised up to such a level as is in excess of the temperature at the transformation point, the temperature of the hot spot is subjected to retention at the transformation point in a sequential manner, starting from such a surface flaw as has the maximum depth. To put it otherwise, such a surface flaw whereof the inherent value of K is high enough, the relation between the depth $d$ of the surface flaw and the value of K at the same mean value of temperature rise becomes non-linear, as shown in FIGS. 11 and 12, and the precision of finding the depth of the surface flaw by taking the degree or the value of temperature rise as a criterion therefor is thus deteriorated.

Next, in the case of detecting the surface flaw in the form of the peak level of the output signal indicated on the radiation dosimeter of the scanning type, it is generally required that the ratio of the signal level $\Delta\theta$ to the noise level $\Delta\theta$m, i.e., the S/N ratio, be in excess of the range of 1.5 - 2. If the S/N < 1.5 or so, it is difficult to discriminate a signal from a noise, and, when a signal is to be detected in a proper manner in such a case, the rate of over-detection may cause a flawless portion to be detected as a flaw in an erroneous manner.

As already set forth above, the noise level $\Delta\theta$m is a synthesized product of non-uniformity of the surface temperature of the slab. Such a noise is generated by a photo-to-electricity converter of a radiation dosimeter of the scanning type. Noise is also generated out of the signal processing system. Also a synthesized noise is generated at approximately 600° - 700° C in surface temperature of the slab. When employing an infrared ray detector of the photoelectron type which is approximately 6° C, when converted into temperature, which is free from being influenced by the mean value of temperature rise $\theta$ itself or the level thereof, hence virtually constant both before and after conducting induction heating. Therefore, such a signal level $\Delta\theta$ is required for detecting a surface flaw on an iron or steel member of such surface temperature which is approximate in value to the temperature of the magnetic transformation point, is required to be in excess of 9° C, in view of the fact of S/N $\geq$ 1.5.

The actualizing power K of the surface flaw, is what is characteristic of the surface flaw, and is virtually free from being influenced by the mean value of temperature rise $\theta$. Therefore, when the minimum depth of the surface flaw (the minimum depth of the harmful defect), selected as an object of detection, is once determined, the value of K of the surface flaw of the said minimum depth is thus determined. Therefore, such a signal level as is required for detecting a surface flaw of the minimum depth is also determines the minimum requirement of the mean value of temperature rise $\theta$min. Therefrom, the following formula can be established.

$$\begin{pmatrix}\text{Minimum requirement of}\\ \text{mean value of tempera-}\\ \text{ture rise } \theta(\text{mm})]\end{pmatrix} = \frac{[\text{Synthesized noise level } \Delta\theta\text{m}] \times [\text{Required S/N ratio}]}{\begin{bmatrix}\text{Value of K of surface flaw}\\ \text{of minimum depth (K)}\end{bmatrix}}$$

For instance, in case the depth of a harmful defect is supposed to be 2mm, the value of K is 0.2, and the noise level × 1.5 (required signal level) is 9° C as mentioned above; therefore, the minimum requirement of the mean value of temperature rise $\theta$min is as shown below:

$$\theta\text{min} = \frac{9}{0.2} = 45[° C]$$

Therefore, a harmful defect of K $\geq$ 0.2 can be properly detected in the case of 50° C in mean value of temperature rise.

However, when the temperature is raised up to such a level as is in excess of the temperature at the magnetic transformation point, the temperature of such a hot spot on the surface flaw-bearing portion is subjected to retention at the said temperature of transformation point. The temperature of the normal portion is caused to rise in the course of the said process. As a result thereof, the inherent actualizing power K (value of K) of the surface flaw is caused to be deteriorated. Therefore, when the temperature is raised by as much as 50° C, in case the surface temperature $T_1$ is of such a value as $T_1 \leq 650°$ C, as shown in FIG. 10, the surface temperature $T_1$ of a surface flaw of K = 0.4 is raised by as much as 50° C in the state of $T_1 = 700°$ C, and, as a result thereof, the value of K is lowered down to the level of 0.1, to thus make it impossible to detect the surface flaw.

To put it otherwise, when the temperature is raised by as much as the mean value of temperature rise $\theta$, that is 50° C, where the surface temperature under such a state is $T_1 \leq 650°$ C, such a signal level $\Delta\theta$ of 20° C which is in excess of the required signal level of 9° C can be used, thus being throughly capable of detecting the surface flow. However, when the temperature is raised by as much as the mean value of temperature rise $\theta$, that is 50° C, with a surface temperature $T_1$ of 700° C, then the signal level $\Delta\theta$ becomes 5° C, which fall short of the required signal level of 9° C, thus making it impracticable to conduct proper detection.

As elucidated in the preceding paragraphs, in such a system wherein a surface flaw is thermally actualized by carrying out induction heating, and the surface flaw is detected by the employment of a radiation thermometer, for example, an infra red thermometer of the scanning type, detection of a surface flaw in the vicinity of the temperature at the magnetic transformation point of an iron or steel member having ferro magnetic substance results in deteriorating both the precision of detecting the presence of a surface flaw and the precision of detecting the depth of the surface flaw.

With an aim specifically set at eliminating the said defects, the present invention was provided for the purpose of detecting with precision the depth of a surface flaw, as well as detecting in an infallible manner the presence of a surface flaw of multifarious iron and steel members of various levels of surface temperature, by controlling the surface temperature of the iron and steel members in advance, before subjecting the iron and steel members to induction heating. In this manner the temperature of the said members is adjusted around the magnetic transformation point thereof, including the high-temperature portion thereof. In this way the process of raising the temperature by as much as a designated mean value of temperature rise, at the time of conducting induction heating can be carried out by as much.

The control of the surface temperature of iron and steel members before conducting induction heating can be effected by the application of either a cooling process or a heating process.

In the case of controlling the surface temperature of an iron or steel member by the application of a heating process, such an iron or steel member whose temperature is the same as, or below, the temperatures at the magnetic transformation point, is heated up to the level of being well in excess of the temperature of the magnetic transformation point. The temperature thus raised by heating is properly kept free from exceeding the temperature level at the magnetic transformation point in the process of raising the temperature by conducting induction heating.

As the means of the said heating, such an induction heating apparatus as is arranged on an on-line base, a conventional heating oven, or the like, besides an induction heating apparatus for detecting a surface flaw, can be selected for this purpose.

In the case of controlling the surface temperature of an iron or steel member by the application of a cooling process, the temperature of the material before being subjected to induction heating is measured and the required range of cooling the surface of the material is determined. By taking the surface temperature of the said material thus measured, the minimum depth of the surface flaw present on the said material (the value of K characteristic of the said surface flaw), to be detected, the required minimum value of temperature rise $\theta$ that has been already determined from the aforementioned synthesized noise level, and the maximum depth of the surface flaw required to be found (the value of K characteristic of the said surface flaw), as the criteria it can be determined under the condition such a high-temperature portion as occurs on the surface flaw-bearing portion having the said maximum depth of flaw is kept free from exceeding the temperature at the magnetic transformation point.

Shown in Table 2 is a table to be referred to for judging whether or cooling is required for the purpose of finding the depth of the surface flaw through the value of temperature rise $\Delta\theta$ at a high-temperature portion. The table includes the case where the actualizing power K (value of K) and the depth of the surface flaw d maintain a linear relationship, as deep as to 10mm in the maximum level of the surface flaw. It indicates the cases where the required minimum mean value of temperature rise $\theta$ is fixed at 50° C, 100° C, or 150° C, and is for such conditions where the instantaneous field of view of a radiation dosimeter of the scanning type 9 is 1mm × 2mm, and the said synthesized noise level $\Delta\theta$ is C.

Table 2

| Value of required temperature rise ($\theta$) | Surface temperature of material before being subjected to cooling ($T_0$) | Whether or not material has been subjected cooling | Surface temperature of material before being subjected to induction heating ($T_1$) |
| --- | --- | --- | --- |
| 50° C | $T_0 \leq 650°$ C | Negative | $T_1 \leq 650°$ C |
|  | $650 < T_0 \leq 750°$ C | Affirmative | $T_1 \leq 650°$ C |
|  | $T_0 > 750°$ C | Negative | $T_1 > 750°$ C |
| 100° C | $T_0 \leq 550°$ C | Negative | $T_1 \leq 550°$ C |
|  | $550 < T_0 \leq 750°$ C | Affirmative | $T_1 \leq 550°$ C |
|  | $T_0 > 750°$ C | Negative | $T_1 > 750°$ C |
| 150° C | $T_0 \leq 450°$ C | Negative | $T_1 \leq 450°$ C |
|  | $450 < T_0 \leq 750°$ C | Affirmative | $T_1 \leq 450°$ C |
|  | $T_0 > 750°$ C | Negative | $T_1 > 750°$ C |

(Magnetic transformation temperature Tc = 750° C

The required minimum mean values of temperature rise, 50° C, 100° C and 150° C, respectively prove to be capable of detecting a surface flaw and finding the depth thereof to the minimum levels of 2mm, 1mm, and 0.5mm, under such conditions that the said noise level $\Delta\theta m$ is 6° C and the S/N ratio required to be detected is 1.5.

FIG. 13 shows such an arrangement of a surface flaw detecing apparatus for iron and steel members as is required for working the method of detection introduced by an embodiment of the present invention. In the drawing, 46 is a temperature control unit of the cooling type arranged in front of a surface flaw detecting apparatus 45 so constituted as shown in FIG. 7, and 47 is a spray head for injecting such a fluid for cooling as highly pressurized water or highly pressurized air over the surface of a slab 48 in a uniform manner.

Reference 49 represent a highly pressurized fluid feed pump, which feeds the spray header 47 with a high-pressure fluid. Reference 50 is a flow rate control valve, which controls the quantity of a cooling fluid.

Reference 51 is a radiation dosimeter provided with a photoelectric conversion system and measures the surface temperature at the center and in the direction of the width of the slab 48 on the input side of the said spray header 47. The reason why the measurement is conducted at the center and in the direction of the width of the slab 48 is that this position is the point of the highest temperature on the slab 48. It goes without saying that the highest temperature in one scanning in the direction of the width of the slab 48 can be so caused as to be deleted by the radiation dosimeter of the scanning type.

Reference 52 is a control unit which controls the degree of opening of the control valve 50 in corresponding to an output signal given by the said radiation dosimeter 51. Reference 53 represents a motor which drives the said pump 49. Reference 54 is a signal processing apparatus which processes an output signal given by the said radiation dosimeter 32. The said slab 48 is a continuously cast slab for the use of a plank. Reference 55 is a descaling apparatus specifically designed for removing a scum present on the surface of the slab 48.

The mean value of temperature rise $\theta$ designated by the surface flaw detecting apparatus 45 is determined in such a manner as is set forth below.

The surface temperature range of the continuously cast slab 48 at the time of its arrival to this apparatus is 20°– 1,200° C, and the temperature at the magnetic transformation point Tc is 750° C. Now that the said slab 48 is made of a plank, the minimum depth of the surface flaw to be detected at this stage is to be 1mm, when the draft percentage at the time of rolling the plank into a product is taken into account. The synthesized noise level $\Delta\theta m$, converted into temperature, of the said radiation dosimeter 32 is 6° C, and the S/N ratio required for discriminating a noise signal $\Delta\theta m$ and a flaw sigal $\Delta\theta$ from each other is 1.5 or less.

The actualizing power K of a surface flaw of 1mm in depth is 0.1 in value at the time induction heating is conducted without exceeding the temperature at the magnetic transformation point, and when measurement of temperature, as well as scanning, is carried out by the radiation dosimeter of the scanning type, at a level of the instantaneous field of view of 1mm × 2mm. The minimum mean value of temperature rise $\theta$ by induction heating, as is required for taking such a high-temperature portion bearing a surface flaw of 1mm in depth, as a peak signal in the output signal given by the radiation dosimeter of the scanning type 32 (or in the flaw signal $\Delta\theta$ given by the said radiation dosimeter), must be as shown below:

$$S/N \geq 1.5, S = K\theta$$

therefore,
$$\theta \geq (1.5N/K)$$

therefrom, the said mean value of temperature rise $\theta$min is formulated as shown below.

$$\theta = 90° C = \frac{1.5 \times 6}{0.1}$$

In the present case, the following formula is adopted.

$$\theta = 100° C$$

Now, suppose the maximum depth of the surface flaw to be subjected to the process of finding the depth of the flaw by the employment of the said surface flaw detecting apparatus 45 is 15mm.

Now that the said mean value of temperature rise cannot be modified in a manner to correspond with the surface temperature of the continuous casting slab 48 to be fed to the series of arranged equipment, the mean value of temperature rise $\theta$ is kept content at the level of 100° C. This is so even in case the surface temperature is subjected to fluctuations in the range of 20° – 1,200° C. with regard to the high-temperature portion of the said surface flaw-bearing portion of 15mm in depth, the surface temperature $T_1$ of the said slab 48 before being subjected to induction heating must be as shown below for the purpose of keeping the temperature free from exceeding the temperature at the magnetic transformation point, 750° C.

$$T_1 + (1 + K)\theta \leq Tc \dots \quad (6)$$

$$T_1 \leq Tc - (1 + K)\theta \dots \quad (7)$$

Here, Tc: Temperature at magnetic transformation point, viz. 750° C
$\theta$: Mean value of temperature rise, viz. 100° C
K: Actualizing power of surface flaw of 15mm in depth, viz. 1.5

The said surface temperature $T_1$ is thus found to be 500° C, by the application of the formula (7) given above.

Therefore, judgment of whether or not cooling is required according to the surface temperature To of the continuously casting slab 48 to be measured by the radiation dosimeter 51 is as shown in Table 3 given below.

Table 3

| Surface temperature Tc of slab 16 | Whether or not cooling is required |
|---|---|
| To ≦ 500° C | Negative |
| 500° C < To ≦ 750° C | Affirmative |
| 750° C < To | Negative |

The surface temperature cooling requirement $\Delta T$ of the slab 48 at the time the cooling is required, is as set forth below.

In case the surface temperature To measured by the radiation dosimeter 51 is in the range of 500° – 750° C, the value of such a surface temperature cooling requirement ΔT is found by the relationship ΔT ≧ To-500 for each slab, or a constant value for cooling the surface temperature is set at a ΔT of 250° C.

In case the surface temperature $T_1$ does not meet the requirement of $T_1 \leq 500°$ C, with regard to the slab 48 before its being subjected to induction heating, due to heat recovery from the interior of the slab in the direction of the thickness thereof in the process of transfer from the spray header 47 to the coil 40, then it goes without saying that the said surface temperature cooling requirement ΔT provided by the spray header 47 is to be set in advance as to be in excess of the said surface temperature cooling requirement.

In the arrangement of the apparatus shown in FIG. 13, the said slab 48 has its surface temperature measured at the center position in the direction of the width thereof, when the slab 48 is fed to the cooling type temperature control unit 46 by the roller table 35. When the surface temperature To is either less than 500° C or over 750° C, the said slab 48 is transferred to the surface flaw detecting unit 45, without being subjected to cooling by the spray header 47, and is subjected to heating in a sequential manner by the said coil 40 by as much as the said designated mean value of temperature rise θ of 10° C, while being transferred in the said coil 40 at constant speed. Then, immediately after the heating, the surface is subjected to scanning and the surface temperature is measured by the radiation dosimeter of the scanning type 32. The signal processing unit 54 carries out detection of the position of the surface flaw by taking the position of the peak of the output signal given by the radiation dosimeter of the scanning type 32 as a criterion therefor. It also determines the depth of the surface flaw by taking the level of the said peak as a criterion therefor.

Meanwhile, if the surface temperature To is within the range of 500° - 750° C, the temperature control unit 52 carries out operation of To-500-α to find the surface temperature cooling requirement ΔT. It does this by taking the surface temperature To at each position of slab 48 in the direction of its transfer to thus carry out proper control of the degree of opening of the valve 50 and the quantity of cooling water in such a manner that the said surface temperature $T_1$ is to be less than 500° C at the time of conducting induction heating.

In this manner the surface temperature $T_1$ of the slab 48 before its being subjected to induction heating is may less than 500° C. It is then subjected to induction heating by the said coil 40 by as much as the said mean value of temperature rise θ of 100° C, while being transferred in the said coil 40. This prevents the temperature of such a high-temperature portion as is possibly caused at a surface flaw-bearing portion of the maximum depth in the flaw. The depth of the said flaw is to be found by reaching a level with is in excess of the temperature at the magnetic transformation point. The surface of the slab 48 immediately after carrying out induction heating is subjected to scanning and the temperature thereof is measured, in the same manner as set forth above. Then, the position of the surface flaw is determined by taking the position of the peak of an output signal given by the radiation dosimeter of the scanning type 32 as a criterion therefor. The depth of the flaw is then judged by taking the level of the peak as a criterion therefor, by using the signal processing unit 54.

Now that, in the case of this method, the depth $d$ of a surface flaw and the actualizing power K are maintained in a proportional manner, the normal performance of the surface flaw detection unit can be obtained in a favorable manner, completely free from deteriorating the precision of surface flaw detection and the precision of surface flaw depth judgment as well.

The arrangement of respective units shown in FIG. 13 is for detecting only the top surface of the slab. However, in case the temperature control unit of the cooling type 46 is provided with a spray header and a radiation dosimeter for the under surface, and the surface flaw detecing unit 45 is provided with an induction heating coil and a radiation dosimeter of the scanning type for the under surface, then both the top surface and the under surface of the slab 48 can be detected in a concurrent manner.

Furthermore, it is practicable that two pairs of the assemblies of the said surface flaw detecting unit 45 and the said temperature control unit of the cooling type 46 are arranged in the direction of transfer of the slab. Such a contrarotating unit which reverses the top surface and the under surface of the slab is arranged in place at an intermediate position between the said pairs of assemblies. This makes the assemblies into a surface flaw detecing unit for the exclusive use of each surface.

Now, when control of the surface temperature of the slab is carried out by the application of a surface cooling process, the effect of energy saving is more or less marred. However, the loss of energy by surface cooling is slight and is less than 1% of the sensible heat of an iron or steel member of such surface temperature and is less than the temperature of the magnetic transformation point or its vicinity. Therefore, the effect of energy saving to be attained in the case of applying a hot charge process or a direct rolling process is kept free from a great deal of loss by the application of the method introduced in the present invention.

In the description given above, a statement is made to the effect than an iron or steel member of such a temperature level as is in excess of the magnetic transformation point is to be subjected intact to induction heating. However, in case the temperature is in excess of the said magnetic transformation point, approximately three times as much power is required for heating to the same mean value of temperature rise, as long as the frequency remains the same. This is mainly due to deterioration of the coil in terms of heating efficiency, and to an increase in value in terms of the depth of penetration.

Therefore, in the case of an iron or steel member of such a temperature level which is in excess of that of the magnetic transformation point, the power requirement can be likewise reduced. This is otherwise by cooling the iron or steel member down to the level of such surface temperature as is shown by the formula (7). The precision of judging the depth of a surface flaw, as well as the precision of detecting the surface flaw, can still be so rendered as to prove satisfactory enough.

Next, given below will be a description of the level of power which is required for raising the surface temperature a predetermined value of temperature rise, by subjecting the surface thereof to induction heating, immediately after subjecting the same to cooling.

It is recommended that a frequency be properly selected in such a manner that the thickness (the depth of penetration of an electric current) of the surface to be heated by the application of an induction heating process corresponds to the minimum depth of a surface flaw.

Figure 14:
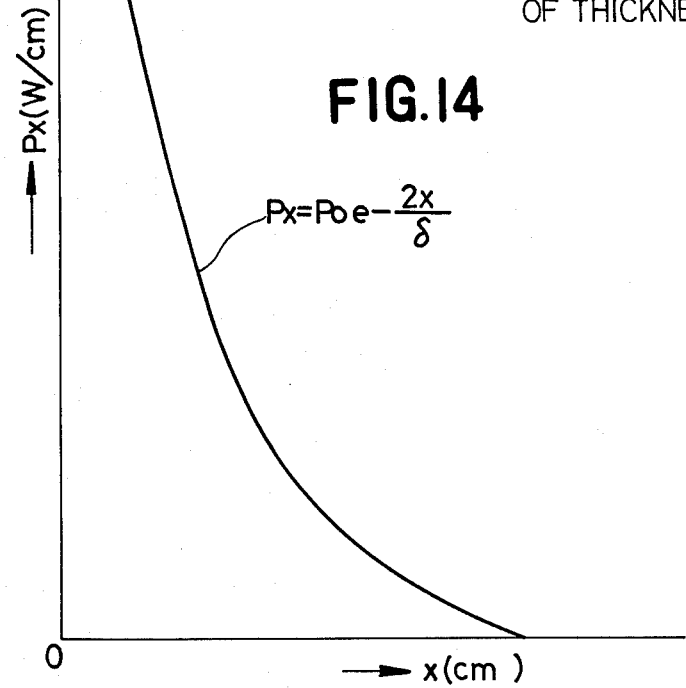
FIG. 14 is a diagram of λ heat distribution in the direction of the thickness of the material by induction heating.

The distribution of the input heat in the direction of the thickness of the metallic material caused by induction heating per unit surface area (1 cm²) of such a portion as is subjected to the induction heating is as shown by the following formula (10) and FIG. 14.

$$Px = Po\, \epsilon^{-\frac{2x}{\delta}}\ [W/cm] \qquad (10)$$

Here, $x$ : Distance of position in the direction of thickness (cm)
$\delta$ : Depth of penetration of electric current (cm)
$\epsilon$ : Base of natural logarithm
Px : Calorie of heat input at the position over the distance of $x$ in the direction of the thickness of material (W/cm)
Po : Calorie of heat input on the surface (x=0) of material (W/cm)

Now, suppose that distribution of temperature of the material in the direction of the thickness thereof, before being subjected to induction heating, is uniform. Assume also that the material is an iron or steel member, and the temperature of the iron or steel member is in the range of approximately 600° – 1,200° C. The thermal conductivity of the iron or steel member is approximately 0.07 (cal/cm.sec.° C). In this case, FIG. 15 shows the distribution of temperature raised in the direction of the thickness thereof. This case is for when the depth of penetration of an electric current $\delta$ is 0.08 (cm), the frequency range is 50KHz through 200KHz at 600°–1,200°. C in temperature range of the iron or steel member, the calorie of heat input Po on the surface is 12,000 [W/cm]. The graph shows one when heat dissipation entails after heating for 0.1 sec. (heat conduction into the interior thereof in the direction of the thickness entails), and also the distribution of temperature raised in the direction of the thickness of the said iron or steel member, with no heat dissipation taken into account. When the heat conduction in the direction of the thickness of the material and the heat dissipation from the surface of the material can be disregarded, as shown in FIG. 15, the surface temperature rises by as much as 175° C. When the heat conduction in the direction of the thickness of the material is taken into accoutn, the temperature rise is only by 78° C. In this case, the input energy on the surface of the material is considerable, compared with the escaping of the energy by radiation. Although it is recognized that the matter is more or less attributable to the lowering of the surface termperatue by radiation, hence virtually negligible. To put it otherwise, under the aforementioned conditions, the value of the input energy per 1cm² of surface area is as shown below:

$$Ps = \int_0^\infty Po\, \epsilon^{-\frac{2x}{\delta}}$$
$$= \frac{\delta}{2} \cdot Po$$
$$= \frac{0.08}{2} \cdot 12{,}000$$
$$= 480\ [w]$$

The quantity of escaping energy Pr(W/cm²) by radiation into the atmosphere through free radiation can virtually be found by the application of the following formula:

$$Pr \approx 5.7\, \epsilon\, (\frac{T}{100})^4 \cdot 10^{-4}\, (\frac{W}{cm^2})$$

Here,
T : Absolute surface temperature (°K)
$\epsilon$ : Radiation factor

Now, suppose the surface temperature of an iron or steel member is 1,273° K (1,000° C), and the radiation factor is 0.8, then, the quantity of escaping of energy Pr is approximately 12W/cm². This value can be disregarded in view of the aforementioned input energy density of 480W/cm².

For preventing heat dissipation in the direction of the thickness of the material at the time of carrying out induction heating, the only thing required is to form a temperature gradient in the direction of the thickness in a reverse manner to the case of carrying out heating. The said temperature gradient in the direction of the thickness in the reverse manner to the case of carrying out heating can be properly formed by spraying water, an atomized liquid, or air over the surface of warm rolled or hot rolled material, followed by cooling the same.

For one thing, in the case of forming the temperature gradient by spraying water and cooling, the distribution of temperature in the direction of the thickness is found in such a manner as is set forth below.

Figure 16:
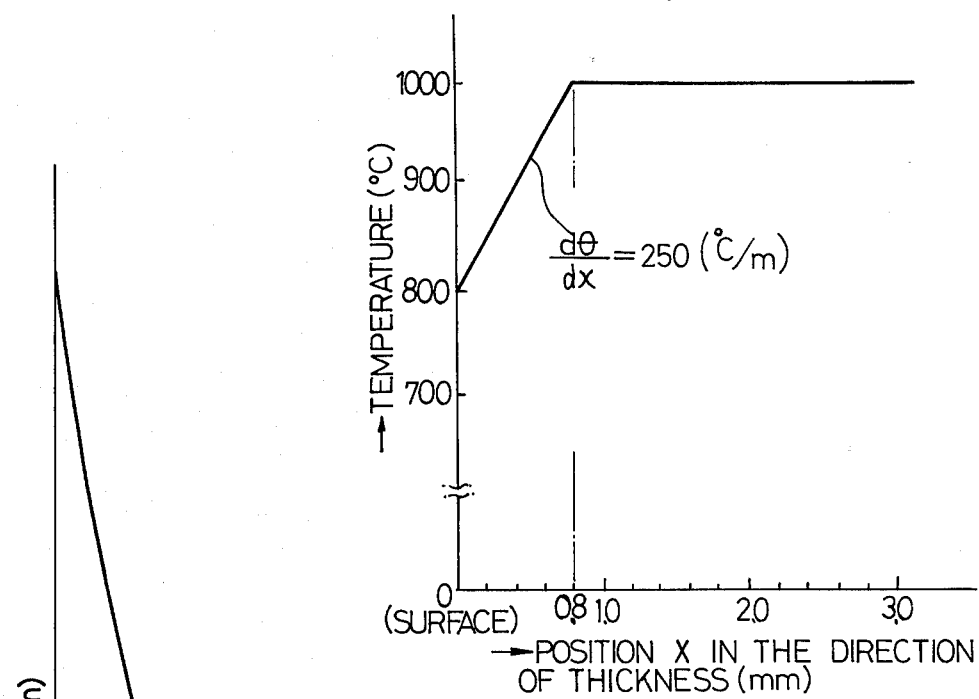
FIG. 16 is a diagram of temperature distribution in the direction of the thickness of the material immediately after cooling the surface temperature by as much as 200° C at the surface temperature of 1,000° C.

| Under such conditions as | |
|---|---|
| Temperature of steel member | 1,000° C |
| Thermal conductivity of steel member | 25KCal/m · hr · ° C |
| Temperature of cooling water | 20° C |
| heat transfer coefficient to cooling water | 8,000KCal/m² · hr · ° C | then the temperature gradient (d$\theta$/dx) in the direction of the thickness of a steel member at the time the surface temperature of the steel member is cooled by as much as 200° C is $$25 \cdot \frac{d\theta}{dx} = 8{,}000 \cdot (1{,}000 - 200 - 20)$$
$$\frac{d\theta}{dx} \approx 247{,}000\ (°\ C/m)$$

hence, approximately 250° C/mm. To put it otherwise, the distribution of temperature in the direction of the thickness of the steel member, immediately after the surface temperature thereof is cooled by as much as 200° C, is as shown in FIG. 16. The maid temperature gradient (db/dx) has its value reduced by thermal condition from the interior of the material in the direction of the thickness thereof, in proportion to the lapse of time after lowering of a designated degree of the surface temperature. Meanwhile, when induction heating is conducted at a frequency that has a distribution of energy which forms the distribution of temperature, as is disregarding heat dissipation, shown in FIG. 15, the quantity of heat to be conducted in the direction of the thickness of the material is considerably reduced.

To put it otherwise, when power is fed as an input and as has the distribution of energy of $$Px = 12{,}000\, \epsilon^{-\frac{x}{0.08}}$$

Figure 17:
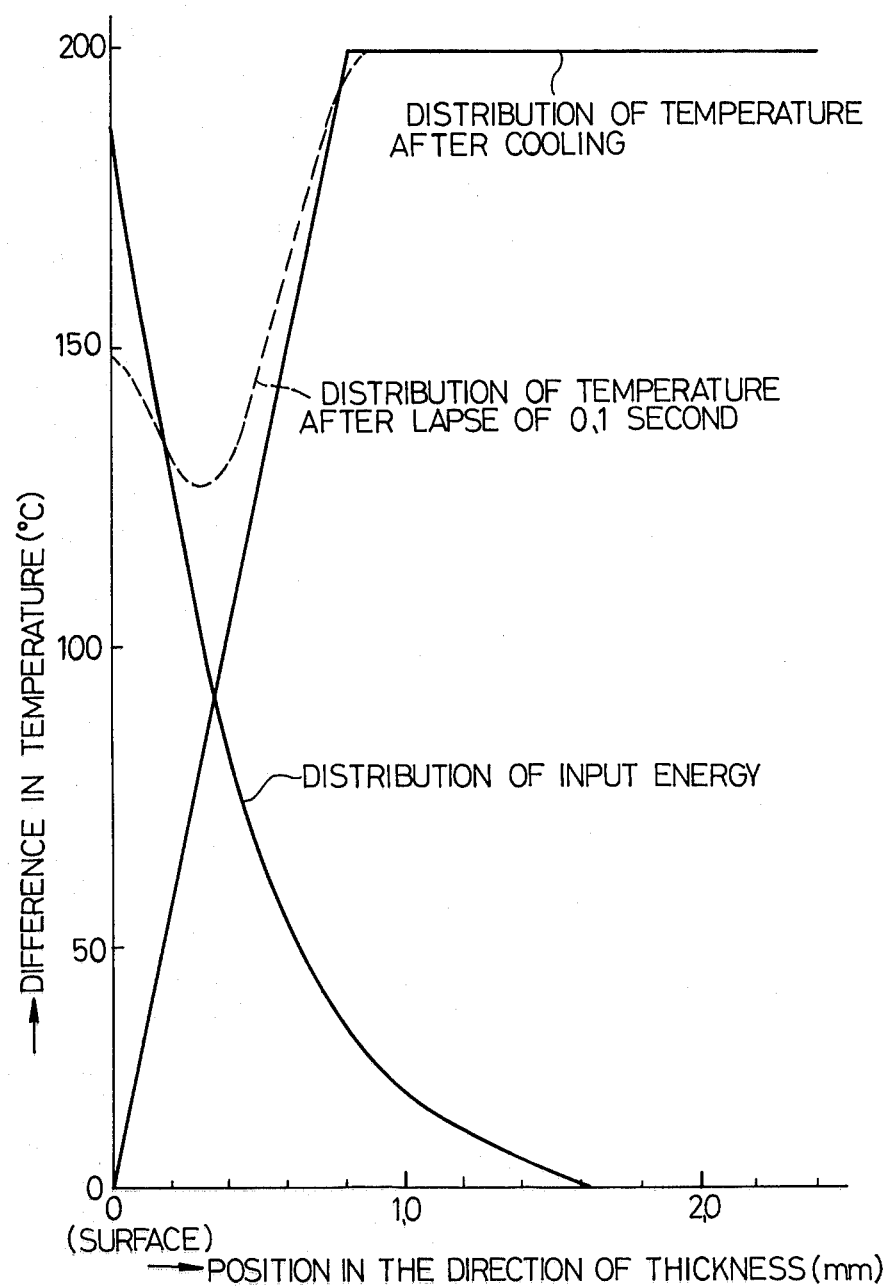
FIG. 17 is a diagram to show the distribution of rising temperature in the direction of the thickness of the material at the time of subjecting the same to induction heating immediately after cooling the surface thereof.

(W/cm) per unit area of the surface material whereon there is formed the temperature gradient in a direction reversed to the direction of heating, as shown in FIG. 16, the distribution of temperature in the direction of the thickness is as shown in FIG. 17.

Therefore, when the surface at any temperature is subjected to induction heating, immediately after cooling thereof, the value of surface temperature rise by induction heating can be increased by approximately two times as much as the case wherein the surface layer of the material is not cooled, wherein the input power is the same for both cases.

This serves to reduce by as much as approximately one half the input electrical power required for finding such a mean set value of temperature rise as is needed at the time of causing to a linear induction current on the surface portion of metallic material. The current will thermally actualize a surface flawbearing portion as a high-temperature portion. It will then be possible to judge the depth of the flaw by taking the value of temperature rise of the said high-temperature portion as a criterion therefor.

Figure 18:
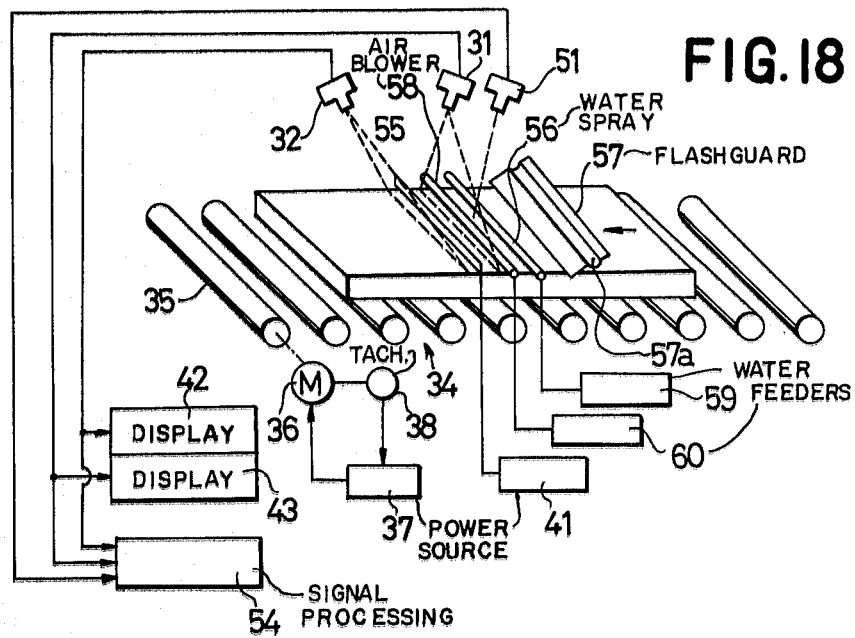
FIG. 18 is a diagram to show an example of the constitution of the surface flaw detecting apparatus with either a hot metallic material or warm metallic material specifically selected as an object of detection.

Shown in FIG. 18 is an example of such a construction of surface flaw detecting unit wherein the surface at any temperature is subjected to induction heating immediately after cooling thereof, whereby the input electrical power required for finding such a mean set value as is required for detecting the depth of a surface flaw is reduced, and the detection of the surface flaw is thus enabled to be conducted at low cost.

The basic constitution of the said surface flaw detecting unit is virtually the same as that of the surface flaw detecting unit 45 shown in FIG. 7.

In FIG. 18, 55 is a transverse flux heating coil which subjects only the top surface of the metallic material 1 to induction heating sequentially in the linear manner in the direction of the width of the said metallic material as the material is transferred by material transfer unit 34. Reference 56 is a cooling water spray header arranged in place in front of the said transverse flux heating coil 55. Reference 57 is a flashboard arranged in place in front of the said cooling water spray header 56 and kept in contact with the top surface of the said metallic material at all time.

Reference 58 is an air blow header arranged between the said coil 55 and the said header 56. References 59 and 60 are respectively a cooling water feeding unit and an air feeding unit. Other numbers represent the same items shown in FIGS. 7 and 13. The cooling water fed through the cooling water spray header 56 is injected in the direction reverse to the direction of material transfer, it subjects the surface of the material to cooling. It runs into a trough of the flashing plate 57 which comes in contact with the material 1 being transferred, and then falls down to the side of a table. Therefore, that portion of the material which does not reach the spot under the header 56 is prevented from being cooled, and only the portion of the material having reached the spot under the header 56 is subjected to quenching. The air blow header 58, on the part thereof, prevents drops of water from reaching a spot under the coil 56.

Table 4

| Induction heating apparatus | | |
|---|---|---|
| 1. Frequency | 50KHz | |
| | Constant | |
| 2. Transverse flux heating coil Size in the direction of the length of material under test | 10 (mm) | |
| Material to be tested | | |
| 1. Such a continuously cast slab piece as has a mill scale on the surface thereof, and the presence of a surface flaw thereof cannot be observed by a visual check from the surface | | |
| 2. Dimensions: Thickness | 200 (mm) | |
| Width | 1,000 (mm) | |

Table 4-continued

| | Length (in the direction of transfer) | 2,000 (mm) | |
|---|---|---|---|
| 3. | Speed of transfer | | 50 (mm/sec) |
| 4. | Surface temperature of material | | |
| | | Cooled | Not cooled |
| Temperature of material before cooling | | 1,100° C | 1,100° C |
| Temperature of material after cooling | | 12 900° C | — |
| Temperature of material before heating | | 950° C | 1,100° C |
| Temperature of material after heating | | 1,050° C | 1,200° C |

The applicant sought to find the interrelation between the surface cooling and the actualizing power under such conditions of experiment as are shown in Table 4 above, and by the employment of such an apparatus as is shown in FIG. 18. In this apparatus the cooling water header 56 was arranged at a position apart from the coil 55 by as much as 50mm. It was found that no appreciable difference was noticed in terms of the actualizing power to be obtained, between the case of subjecting the surface to cooling and the case of subjecting the surface to no cooling at all. To put it otherwise, the only difference the two cases showed in is that, in the case of subjecting the surface to cooling, the input electric power required for obtaining the mean set value of 100° C was 120KW. An input electric power of 240KW was required for obtaining the mean set value of 100° C, without subjecting the surface to cooling at all. Besides, the temperature gradient formed in the direction of the thickness in the vicinity of the surface of a steel member of approximately 1,100° C, when the said steel member was in the state of being exposed to natural cooling, was approximately 5.6° C/mm, and the temperature gradient of the said value proved virtually ineffective in preventing heat dissipation in the direction of the thickness.

As described in details in the preceding paragraphs, the method of detecting a surface flaw introduced in the present invention enables the level of the depth of a surface flaw of metallic material to be found in a proper manner, irrespective that the metallic material is a hot rolled one or a cold rolled one. Therefore, any surface flaw can be removed effectively and efficiently enough at a minimum metal loss, by providing a surface flaw removing process with the information regarding the presence of the surface flaw, the planar position of the surface flaw, and the depth of the surface flaw as well. Hence improves economical effects can be achieved thereby.

What is claimed is:

1. A method for detecting a surface defect or flaw of metallic material, comprising the steps of:
   detecting the surface temperature of the metallic material in a linear manner;
   subjecting the surface layer of the metallic material to high-frequency induction heating;
   detecting the surface temperature of the same portion of the metallic material as that detected before induction heating;
   determining a deviation signal between the surface temperature detected before and after induction heating;
   determining a mean value signal of temperature rise from said deviation signal; and determining the depth of the surface defect or flaw as a function of the ratio of the deviation signal to the mean value signal of temperature rise.

2. The method of claim 1 wherein the surface layer of the metallic material is heated by a predetermined mean value of temperature rise sufficient to keep the high-temperature portion thereof from being in excess of the temperature of the magnetic transformation point or Curie point.

3. The method of claim 2 wherein the metallic material is iron or steel.

4. The method of claim 1 and further comprising the step of cooling the metallic material prior to subjecting it to induction heating.

5. A method for detecting a surface flaw of metallic material comprising the steps of:
   transferring a metallic material to be tested at a constant speed;
   scanning a surface portion of said metallic material with a first temperature distribution detector to detect a first temperature distribution of said surface portion;
   induction heating said surface portion with a high frequency induction coil;
   scanning said heated surface portion with a second temperature distribution detector to detect a second temperature distribution of said heated surface portion;
   determining a deviation signal between said first and second temperature distributions to find the depth of a surface flaw on said surface portion,
   determining a mean value signal of temperature rise from said deviation signal; and
   taking the ratio of said deviation signal to said mean value signal of temperature rise to determine the depth of a surface flaw on said surface portion.

6. A method for detecting a surface flaw of metallic material, comprising the steps of:
   transferring a metallic material to be tested at a constant speed;
   scanning a surface portion of said metallic material with a first radiation detector to measure the temperature of said surface portion;
   cooling said surface portion with a temperature control unit;
   heating said surface portion of an induction coil by a predetermined mean value of temperature rise, the relationship between the cooling and heating being to prevent a temperature above the magnetic transformation point;
   scanning said surface portion with a second radiation detector to measure the temperature of said heated surface portion; and
   taking a peak signal from said first and second measured temperatures as a criterion for determining the depth of a surface flaw of said surface portion.

* * * * *